United States Patent
Miyazaki et al.

(10) Patent No.: US 10,029,982 B2
(45) Date of Patent: Jul. 24, 2018

(54) LIGHT ABSORPTIVE COMPOUND, POLYMER COMPOSITION CONTAINING THE COMPOUND, POLYMER FILM, AND CURED LAYER

(71) Applicant: Sumitomo Chemical Company, Limited, Tokyo (JP)

(72) Inventors: Katsuaki Miyazaki, Osaka (JP); Haruki Okawa, Niihama (JP); Daichi Fujimoto, Osaka (JP); Shinnosuke Yoshioka, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 22 days.

(21) Appl. No.: 15/390,965

(22) Filed: Dec. 27, 2016

(65) Prior Publication Data
US 2017/0183304 A1   Jun. 29, 2017

(30) Foreign Application Priority Data

Dec. 28, 2015 (JP) .................. 2015-256889

(51) Int. Cl.
| | | |
|---|---|---|
| *C08F 2/50* | (2006.01) | |
| *C08F 2/46* | (2006.01) | |
| *C08G 61/04* | (2006.01) | |
| *C07D 207/20* | (2006.01) | |
| *C08J 5/18* | (2006.01) | |
| *C08K 5/3415* | (2006.01) | |
| *C09J 11/06* | (2006.01) | |
| *C09J 133/08* | (2006.01) | |
| *G02B 5/22* | (2006.01) | |

(52) U.S. Cl.
CPC .............. *C07D 207/20* (2013.01); *C08J 5/18* (2013.01); *C08K 5/3415* (2013.01); *C09J 11/06* (2013.01); *C09J 133/08* (2013.01); *G02B 5/223* (2013.01); *C08J 2333/08* (2013.01)

(58) Field of Classification Search
CPC ....... C07D 207/20; C09J 11/06; C09J 133/08; C08J 5/18; C08J 2333/08; G02B 5/223
USPC ........... 522/75, 74, 71, 1, 189, 184, 6; 520/1
See application file for complete search history.

(56) References Cited

U.S. PATENT DOCUMENTS

2017/0152391 A1 * 6/2017 Miyamoto ................. B41J 2/01

FOREIGN PATENT DOCUMENTS

| JP | 2006308936 A | 11/2006 | |
| WO | WO-2015174402 A1 * | 11/2015 | ................ B41J 2/01 |

* cited by examiner

*Primary Examiner* — Jessica Whiteley
(74) *Attorney, Agent, or Firm* — Panitch Schwarze Belisario & Nadel LLP

(57) ABSTRACT

The object of the present invention is to provide a light absorptive compound which is capable of selectively absorbing light around a wavelength of 400 nm, and is excellent in solubility in various solvents and/or affinity with hydrophobic substances. Also, the object of the present invention is to provide an optical film containing such a light absorptive compound, and a cured layer. A compound represented by the following formula (I):

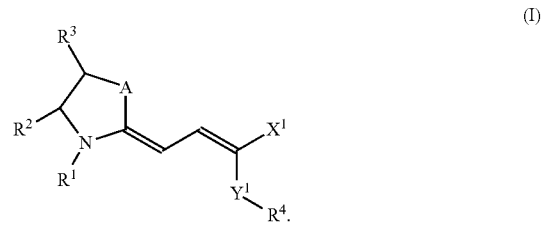

14 Claims, 1 Drawing Sheet

LIGHT ABSORPTIVE COMPOUND, POLYMER COMPOSITION CONTAINING THE COMPOUND, POLYMER FILM, AND CURED LAYER

BACKGROUND OF THE INVENTION

Field of the Invention

The present invention relates to a light absorptive compound, a polymer composition containing the compound, a polymer film, and a cured layer.

Description of the Related Art

Various members, for example, display elements such as an organic EL element and a liquid crystal cell, and optical films such as a polarizing plate and a retardation plate are used for flat panel display devices (FPD) such as an organic EL display device and a liquid crystal display device. A problem of deterioration due to ultraviolet rays (UV) may be caused for the reason that materials for an organic EL compound and a liquid crystal compound used for these members are organic matter. Measures to add an ultraviolet absorbing agent to a protection film of a polarizing plate used for the display devices are taken for solve such a problem. For example, in JP-A-2006-308936, prevention of the members against deterioration is intended by adding a UV absorbing agent to a protection film of a polarizing plate used for these display devices.

In recent years, a problem of fatigue and failure of eyesight in displays is caused when displays are visually recognized for a long time, and the blue light cutting function of cutting short-wavelength visible light has been considered as measures against the above problem.

On the other hand, it is preferable for favorable color expression to absorb light around a wavelength of 430 nm as blue light with difficulty. Thus, a light absorbing agent capable of selectively absorbing light around a wavelength of 400 nm is necessary.

Also, such a light absorbing agent needs to be dissolved in a pressure-sensitive adhesive or a solvent. When solubility of a light absorbing agent is insufficient, for example, in heating and stretching an optical film such as a retardation film after the light absorbing agent is added to the film, the light absorbing agent bleeds out on the surface of the film, so that light absorbency cannot sufficiently be developed. Thus, it is necessary to be excellent in affinity with hydrophobic substances and in solubility in various solvents for being used as a light absorbing agent.

SUMMARY OF THE INVENTION

Then, an object of the present invention is to provide a light absorptive compound which is capable of selectively absorbing light around a wavelength of 400 nm, and is excellent in solubility in various solvents and/or affinity with hydrophobic substances. Also, another object of the present invention is to provide an optical film containing such a light absorptive compound, and a pressure-sensitive adhesive.

The present invention provides the following appropriate aspects of [1] to [12].

[1] A compound represented by formula (I) below:

[Chemical Formula 1]

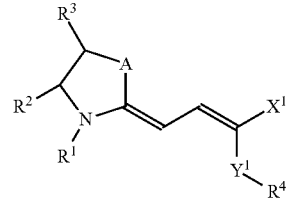

(I)

(In the formula (I),

A denotes a methylene group, a secondary amino group, an oxygen atom or a sulfur atom, $R^1$ denotes a hydrogen atom or an alkyl group with a carbon number of 1 to 10; and when the alkyl group has at least one methylene group, at least one of the methylene groups is optionally substituted with an oxygen atom or a sulfur atom, $R^2$ and $R^3$ independently denote a hydrogen atom or an alkyl group with a carbon number of 1 to 12, $R^4$ denotes an alkyl group with a carbon number of 3 to 50 or an alkyl group with a carbon number of 3 to 50 having at least one methylene group, in which at least one of the methylene groups is substituted with an oxygen atom, and a substituent may be bonded to a carbon atom in the alkyl group, $X^1$ denotes an electron-withdrawing group, $Y^1$ denotes —CO—, —COO—, —OCO—, —O—, —S—, —$NR^5$—, —$NR^6CO$— or —$CONR^7$—, and $R^5$, $R^6$ and $R^7$ independently denote a hydrogen atom, an alkyl group with a carbon number of 1 to 6 or a phenyl group.).

[2] The compound according to [1], in which $R^4$ in the formula (I) is an alkyl group with a carbon number of 3 to 12 having a branched structure.

[3] The compound according to [1], in which the compound represented by the formula (I) is represented by formula (I-I) below:

[Chemical Formula 2]

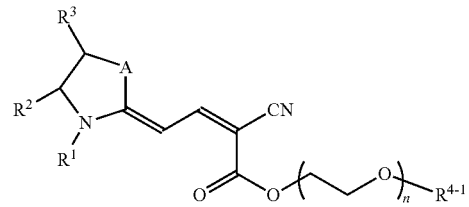

(I-I)

(In the formula (I-I), $R^{4-1}$ denotes an alkyl group with a carbon number of 1 to 6, n denotes an integer of 1 to 10, and A, $R^1$, $R^2$ and $R^3$ are the same as in the formula (I).).

[4] The compound according to [3], in which the compound represented by the formula (I-I) is represented by formula (I-II) below:

[Chemical Formula 3]

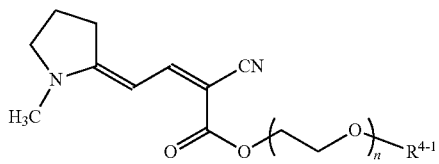
(I-II)

(In the formula (I-II), $R^{4-1}$ and n are the same as in the formula (I-I).).

[5] A polymer composition comprising the compound according to any one of [1] to [4] and a polymer.

[6] The polymer composition according to [5], in which the polymer is at least one kind selected from the group consisting of poly(meth)acrylate, polyurethane, polyester, polycarbonate, polycycloolefin and triacetyl cellulose.

[7] The polymer composition according to [5] or [6], in which the polymer is a copolymer which has as a constitutional unit a (meth)acrylate monomer (A-1) represented by formula (A-1) below:

[Chemical Formula 4]

(A-1)

(In the formula (A-1), $R^p$ denotes a hydrogen atom or a methyl group, $R^q$ denotes an alkyl group or an aralkyl group with a carbon number of 1 to 20, in which a hydrogen atom constituting the alkyl group or the aralkyl group is optionally substituted with $-O-(C_2H_4O)_n-R^r$, n denotes an integer of 0 to 4, and $R^r$ denotes an alkyl group with a carbon number of 1 to 12 or an aryl group with a carbon number of 1 to 12.)
and a (meth)acrylic monomer (A-2) having a hydroxyl group, and which is poly(meth)acrylate with a weight-average molecular weight of 500000 to 2000000, and the polymer composition contains 0.01 to 5 parts by mass of a crosslinking agent and 0.01 to 10 parts by mass of the compound with respect to 100 parts by mass of the polymer.

[8] A polymer film comprising the polymer composition according to any one of [5] to [7].

[9] A pressure-sensitive adhesive comprising the polymer composition according to [7].

[10] A photopolymerizable composition composing a monomer having a photopolymerizable functional group, a photopolymerization initiator, a solvent and the compound according to any one of [1] to [4].

[11] A cured layer comprising a cured material of the photopolymerizable composition according to [10], which satisfies formulae (1) to (3) below:

$$0 \text{ nm} \leq Re < 10 \text{ nm} \quad (1)$$

$$A(420)/A(400) \leq 0.4 \quad (2)$$

$$Hz \leq 3 \quad (3)$$

(In the formula (1),

Re denotes an in-plane retardation value at a wavelength of 550 nm,

A(420) in the formula (2) denotes absorbance at 420 nm and A(400) denotes absorbance at 400 nm, and Hz in the formula (3) denotes turbidity.).

[12] An image display device comprising at least one kind selected from the group consisting of the polymer film according to [8], the pressure-sensitive adhesive according to [9], and the cured layer according to [11].

The present invention can provide a light absorptive compound which is capable of selectively absorbing light around a wavelength of 400 nm, and is excellent in solubility in various solvents and/or affinity with hydrophobic substances. Also, the present invention can provide an optical film containing such a light absorptive compound, and a pressure-sensitive adhesive.

DETAILED DESCRIPTION OF THE PREFERRED EMBODIMENTS

Figure 1:
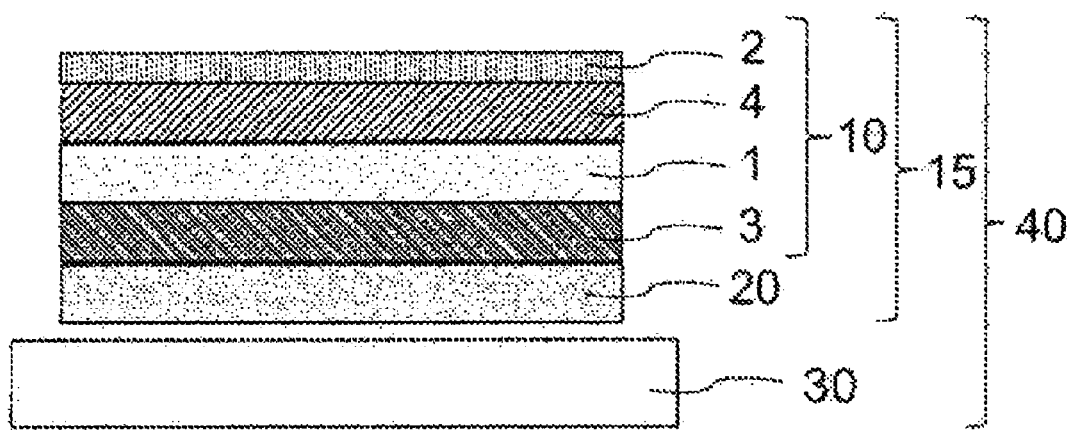
FIG. 1 is a schematic cross-sectional view showing an example of a layer structure of an optical laminated body in an embodiment of the present invention.

An embodiment of the present invention provides a compound (I) represented by the following formula (I):

[Chemical Formula 5]

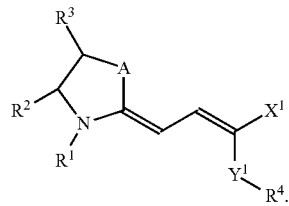
(I)

In the formula (I), A denotes a methylene group, a secondary amino group, an oxygen atom or a sulfur atom, preferably a methylene group, a secondary amino group or an oxygen atom from the viewpoint of developing high light-selective absorbency.

In the formula (I), $R^1$ denotes a hydrogen atom or an alkyl group with a carbon number of 1 to 10, preferably an alkyl group with a carbon number of 1 to 8, more preferably a carbon number of 1 to 5, furthermore preferably a carbon number of 1 to 3 from the viewpoint of developing high light-selective absorbency. Here, when the alkyl group has at least one methylene group, at least one of the methylene groups is optionally substituted with an oxygen atom or a sulfur atom. Examples of the alkyl group include a methyl group, an ethyl group, a n-propyl group, an isopropyl group, a n-butyl group, a tert-butyl group, a n-hexyl group, a n-octyl group, a n-decyl group, a methoxy group, an ethoxy group and an isopropoxy group.

In the formula (I), $R^2$ and $R^3$ independently denote a hydrogen atom or an alkyl group with a carbon number of 1 to 12, preferably a hydrogen atom or an alkyl group with a carbon number of 1 to 10, more preferably a hydrogen atom or an alkyl group with a carbon number of 1 to 8, furthermore preferably a hydrogen atom or an alkyl group with a carbon number of 1 to 5, particularly preferably a hydrogen atom or an alkyl group with a carbon number of 1 to 3 from the viewpoint of developing high light-selective absorbency.

In the formula (I), $R^4$ denotes an alkyl group with a carbon number of 3 to 50 or an alkyl group with a carbon number of 3 to 50 having at least one methylene group, in which at least one of the methylene groups is substituted with an oxygen atom.

With regard to an alkyl group with a carbon number of 3 to 50 in $R^4$, the carbon number is preferably from 8 to 45 (such as from 10 to 45), more preferably from 12 to 40, furthermore preferably from 13 to 35, particularly preferably from 14 to 30 from the viewpoint of affinity with hydrophobic substances, solubility in hydrophobic solvents and economy in production. Incidentally, a substituent may be bonded to a carbon atom in the alkyl group.

An alkyl group with a carbon number of 3 to 50 having at least one methylene group in $R^4$ denotes an alkyl group with a carbon number of preferably 3 to 40, more preferably 4 to 35, particularly preferably 5 to 30 from the viewpoint of affinity with hydrophobic substances, solubility in hydrophobic solvents and economy in production. Here, in an alkyl group with a carbon number of 3 to 50 having at least one methylene group, at least one of the methylene groups is substituted with an oxygen atom; and examples include an ethoxy group, a propoxy group and a 2-methoxyethoxymethyl group. Also, examples include polyethylene glycol groups such as a diethylene glycol group and a triethylene glycol group, and polypropylene glycol groups such as a dipropylene glycol group and a tripropylene glycol group.

Also, a substituent may be bonded to a carbon atom in the alkyl group of $R^4$. Examples of the substituent include a halogen atom, an alkyl group with a carbon number of 1 to 6, a cyano group, a nitro group, an alkylsulfinyl group with a carbon number of 1 to 6, an alkylsulfonyl group with a carbon number of 1 to 6, a carboxyl group, a fluoroalkyl group with a carbon number of 1 to 6, an alkoxy group with a carbon number of 1 to 6, an alkylthio group with a carbon number of 1 to 6, an N-alkylamino group with a carbon number of 1 to 6, an N,N-dialkylamino group with a carbon number of 2 to 12, an N-alkylsulfamoyl group with a carbon number of 1 to 6, and an N,N-dialkylsulfamoyl group with a carbon number of 2 to 12.

When $R^4$ is an alkyl group with a carbon number of 3 to 50, $R^4$ is more preferably an alkyl group with a carbon number of 3 to 12 having a branched structure, furthermore preferably an alkyl group with a carbon number of 6 to 10 having a branched structure from the viewpoint of affinity with hydrophobic substances and solubility in hydrophobic solvents.

Here, the alkyl group having a branched structure denotes an alkyl group in which at least one of carbon atoms in the alkyl group is tertiary carbon or quaternary carbon. Specific examples of the alkyl group with a carbon number of 3 to 12 having a branched structure include alkyl groups having the following structures.

[Chemical Formula 6]

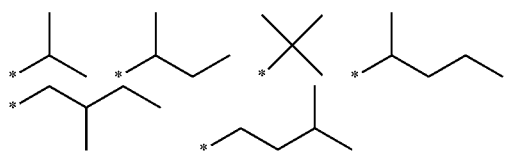

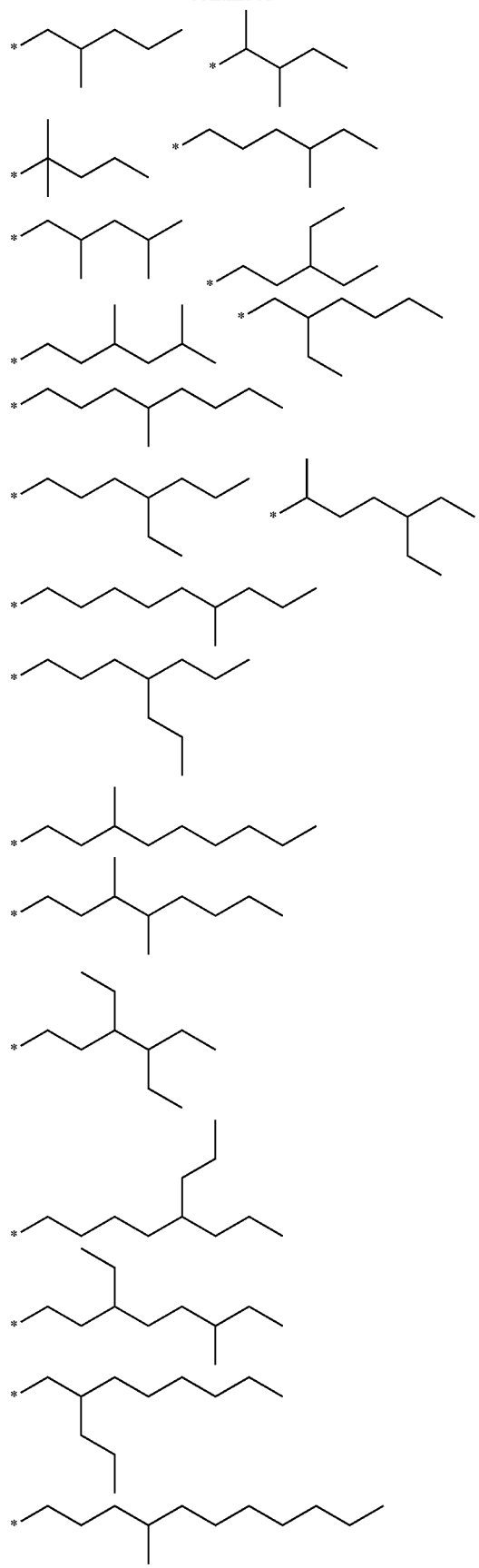

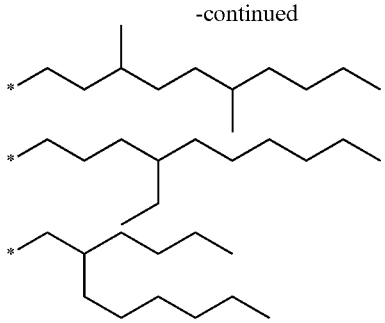

* denotes a connected portion.

In the formula (I), $X^1$ denotes an electron-withdrawing group. From the viewpoint of improving light-selective absorbency, $X^1$ is preferably —$NO_2$, —CN, —$COR^8$, —$COOR^9$, —$OR^{10}$, halogen atoms (—F, —Cl, —Br and —I), —$CSR^{11}$, —$CSOR^{12}$ or —$CSNR^{13}$, more preferably a nitro group, a cyano group or —$COOR^9$, furthermore preferably a cyano group or —$COOR^9$. Here, $R^8$, $R^9$, $R^{10}$, $R^{11}$, $R^{12}$ and $R^{13}$ independently denote a hydrogen atom, an alkyl group with a carbon number of 1 to 6, for example, with a carbon number of 2 to 5, or a phenyl group.

In the formula (I), $Y^1$ denotes —CO—, —COO—, —OCO—, —O—, —S—, —$NR^5$—, —$NR^6$CO—, —$CONR^7$— or —CS—, preferably —CO—, —COO—, —OCO— or —O—, more preferably —CO—, —COO— or —OCO— from the viewpoint of improving light-selective absorbency. Here, $R^5$, $R^6$ and $R^7$ independently denote a hydrogen atom, an alkyl group with a carbon number of 1 to 6, for example, with a carbon number of 2 to 5, or a phenyl group.

In a preferable embodiment of the present invention, the compound (I) represented by the formula (I) is preferably represented by the following formula (I-I):

[Chemical Formula 7]

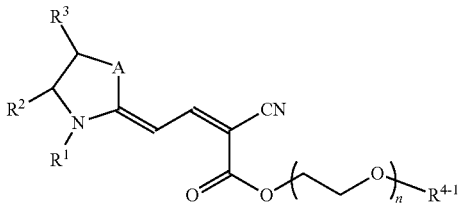

(I-I)

from the viewpoint of being excellent in solubility in various solvents and/or affinity with various compounds.

In the formula (I-I), $R^{4-1}$ denotes an alkyl group with a carbon number of 1 to 6, preferably an alkyl group with a carbon number of 2 to 5, more preferably an alkyl group with a carbon number of 3 to 4.

n denotes an integer of 1 to 10, preferably an integer of 1 to 8, more preferably an integer of 1 to 6, such as an integer of 1 to 4, particularly an integer of 1 to 3 from the viewpoint of being excellent in solubility in various solvents and/or affinity with various compounds. Incidentally, when n falls within the range, light absorbency per one part by mass is improved, and even though the compound (I) contained in a member constituting an optical laminated body is small in amount, the blue light cutting function can be developed. The function of pressure sensitive adhesion is hindered with difficulty when the compound (I) is contained in a pressure-sensitive adhesive. Further, the optical function as a protection film is hindered with difficulty when the compound (I) is contained in a protection film.

A, $R^1$, $R^2$ and $R^3$ are the same as in the formula (I).

In a more preferable embodiment of the present invention, the compound represented by the formula (I-I) is more preferably represented by the following formula (I-II):

[Chemical Formula 8]

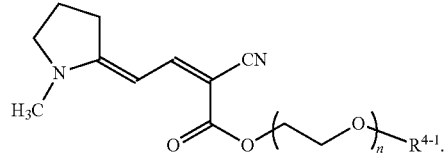

(I-II)

In the case of being the compound represented by the formula (I-II), the compound represented by the formula (I-I) is excellent in solubility in various solvents and/or affinity with various compounds so that the compound is easily dissolved uniformly in solvents, and exhibits amphiphilicity due to excellent affinity with various compounds. Accordingly, when the compound is contained in a member constituting an optical laminated body, a bleed out is caused with difficulty and the light absorption function can be stably exerted.

In the formula (I-II), $R^{4-1}$ and n are the same as in the formula (I-I).

The compound (I) is excellent in solubility in various solvents and/or affinity with various compounds. Examples of the solvents include alcohol solvents such as methanol, ethanol, ethylene glycol, isopropyl alcohol, 1-butanol, 2-butanol, propylene glycol, methylcellosolve, butylcellosolve and propylene glycol monomethyl ether; ester solvents such as ethyl acetate, butyl acetate, ethylene glycol methyl ether acetate, γ-butyrolactone, propylene glycol monomethyl ether acetate and ethyl lactate; ketone solvents such as acetone, 2-butanone, cyclopentanone, cyclohexanone, methyl amyl ketone and methyl isobutyl ketone; aliphatic hydrocarbon solvents such as pentane, hexane and heptane; aromatic hydrocarbon solvents such as toluene, xylene and mesitylene; nitrile solvents such as acetonitrile; ether solvents such as tetrahydrofuran, dimethoxyethane and 1,4-dioxane; and chlorinated hydrocarbon solvents such as dichloromethane, chloroform and chlorobenzene.

The solvents include hydrophilic solvents and hydrophobic solvents. For example, alcohol solvents are generally solvents with hydrophilic property, depending on its carbon number. On the other hand, aliphatic hydrocarbon solvents such as pentane, hexane and heptane are generally solvents with hydrophobic property. In the case of being contained in polymer films such as a pressure-sensitive adhesive sheet and an optical film, the compound (I) is preferably soluble in hydrophilic solvents or hydrophobic solvents, more preferably soluble in hydrophilic solvents and hydrophobic solvents, namely, the compound (I) preferably has amphiphilicity from the viewpoint of causing a bleed out with difficulty and being capable of extending selectivity of solvents.

The compound (I) preferably satisfies the following formula (a).

$$\varepsilon(420)/\varepsilon(400) \leq 0.4 \qquad (a)$$

In the formula (a), the value of ε(420)/ε(400) expresses the intensity of absorption at a wavelength of 400 nm to the intensity of absorption at a wavelength of 420 nm, and the smaller value shows more peculiar absorption in a wavelength region around 400 nm as compared with absorption in a wavelength region around 420 nm. The smaller value offers a transparent compound with less yellowness.

When the compound (I) satisfies the formula (a), light with a wavelength of 420 nm is absorbed with difficulty and also blue visible light is absorbed with difficulty while light with a wavelength of 400 nm is absorbed, so that the compound (I) of the present invention can be provided as a light absorbing agent having the blue light cutting function and hindering favorable color presentation with difficulty, and can be used as a light-selective absorptive compound. In addition, in the case of an optical laminated body containing the compound (I), a member constituting an optical laminated body (for example, an optical film such as a retardation film, and display elements such as an organic EL element and a liquid crystal display element) can be restrained from deteriorating in performance due to short-wavelength visible light (that is, light around a wavelength of 400 nm). The value of ε(420)/ε(400) in the compound (I) is preferably 0.4 or less, more preferably 0.25 or less, furthermore preferably 0.2 or less, particularly preferably 0.15 or less, especially preferably 0.1 or less, greatly preferably 0.05 or less, for example, 0.03 or less. The lower limit thereof is not particularly limited but preferably ordinarily 0.005 or more from the viewpoint of maintaining absorptivity around 400 nm by the compound (I). In an appropriate embodiment of the present invention, the value of ε(420)/ε(400) is from 0.01 to 0.1.

Also, the compound (I) preferably satisfies the following formulae (b) and (c) in addition to the formula (a).

$$\lambda max < 420 \text{ nm} \tag{b}$$

$$\varepsilon(400) \geq 40 \tag{c}$$

In the formula (b), λmax denotes maximum absorption wavelength of the compound (I). In the formula (c), ε(400) denotes gram absorption coefficient at a wavelength of 400 nm, and the unit of gram absorption coefficient is defined by L/(g·cm).

In the case of satisfying the formulae (b) and (c), the maximum absorption of the compound (I) exists on the shorter-wavelength side than 420 nm and the compound (I) exhibits high absorption in the vicinity of a wavelength of 400 nm. The compound (I) satisfies such formulae, so that a member such as a polymer film or a pressure-sensitive adhesive containing the compound (I) affects display characteristics with difficulty to allow high light resistance. In the present invention, the maximum absorption λmax of the compound (I) is more preferably 415 nm or less, furthermore preferably 410 nm or less.

Also, in the case of satisfying the formula (c), the compound (I) has high light absorbency so that even though the compound (I) contained in a member constituting an optical laminated body is small in amount, the blue light cutting function can be developed. The function of pressure sensitive adhesion is hindered with difficulty when the compound (I) is contained in a pressure-sensitive adhesive. Further, the optical function as a protection film is hindered with difficulty when the compound (I) is contained in a protection film. The value of ε(400) is more preferably 60 or more, furthermore preferably 80 or more, particularly preferably 100 or more. Incidentally, the value of ε(400) is ordinarily 500 or less.

The compound represented by the formula (I-II) can be produced in such a manner that, for example, 2-methylpyrroline is made by a methylating agent into a 1,2-dimethyl pyrrolinium salt, which is subsequently reacted with N,N'-diphenylformamidine and finally reacted with an active methylene compound in the presence of acetic anhydride and an amine catalyst. Also, commercially available products as these compounds may be used. The compounds represented by the formulae (I) and (I-I) can be produced similarly.

In another embodiment of the present invention, a polymer composition containing the compound (I) and a polymer is provided (hereinafter, also referred to as 'a polymer composition of the present invention'). The use of the polymer composition allows various members constituting an optical laminated body. Such an optical laminated body can develop the blue light cutting function because of containing the compound (I) excellent in light absorbency and light-selective absorbency. In addition, it has been found out this time that the performance of a display element and an optical film as a component member of FPD deteriorates due to not only ultraviolet rays but also visible light in a short-wavelength region, that is, light around a wavelength of 400 nm; however, a member constituting an optical laminated body, which is contained in an image display device, can be restrained from deteriorating due to short-wavelength visible light. Examples of the member constituting an optical laminated body include a pressure-sensitive adhesive and a polymer film. Examples of the polymer film include optical films such as a polarizing plate and a retardation film, a protection film, a pressure-sensitive adhesive sheet and a front plate. Incidentally, the polymer contained in the polymer composition of the present invention can be selected in accordance with a member to be produced.

Figure 2:
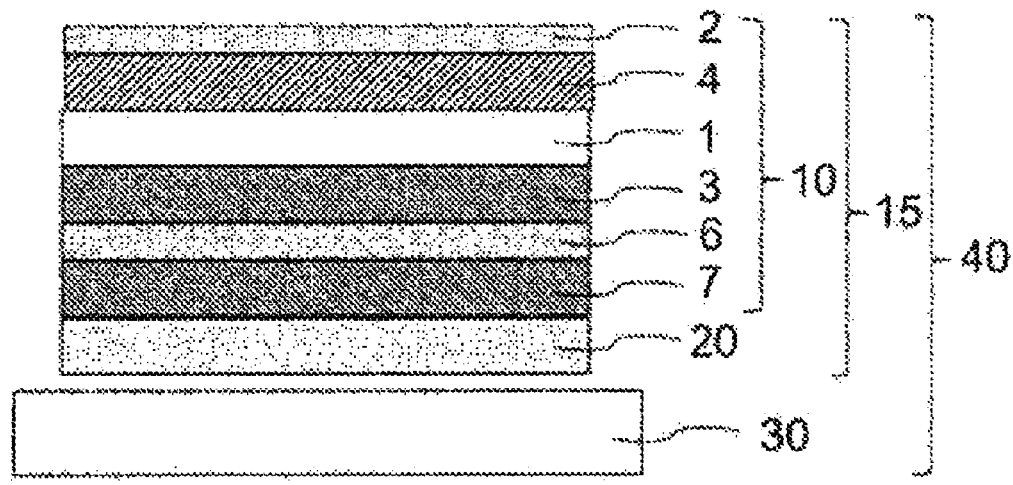
FIG. 2 is a schematic cross-sectional view showing an example of a layer structure of an optical laminated body in an embodiment of the present invention.

Here, with regard to the optical laminated body, examples of several appropriate layer structures are shown by the schematic cross-sectional views in FIGS. 1 and 2. In the example shown in FIG. 1, a first protection film 4 having a surface-treated layer 2 is stuck to one surface of a polarizing plate 1, which is reverse to the surface-treated layer 2, and a second protection film 3 is stuck to the other surface of the polarizing plate 1 to form a polarizing plate 10. A pressure-sensitive adhesive sheet 20 is placed on the outside of the second protection film 3 constituting the polarizing plate 10 to form a polarizing plate 15 with a pressure-sensitive adhesive. Then, the reverse surface of the pressure-sensitive adhesive sheet 20 to the polarizing plate 10 is stuck to an image display element 30 to form an optical laminated body 40. Such an optical laminated body can be used for an image display device. Incidentally, a member containing the compound (I) is preferably disposed on the more visible side than image display elements such as an optical film and an organic EL element that are easily deteriorated. Such disposition allows the function of a member, which is easily deteriorated, to be restrained from being lowered.

In the example shown in FIG. 2, a first protection film 4 having a surface-treated layer 2 is stuck to one surface of a polarizing plate 1, which is reverse to the surface-treated layer 2, and a second protection film 3 is stuck to the other surface of the polarizing plate 1, and a retardation film 7 is stuck to the outside of the second protection film 3 with an interlayer pressure-sensitive adhesive 6 interposed therebetween to form a polarizing plate 10. A pressure-sensitive adhesive sheet 20 is placed on the outside of the retardation film 7 constituting the polarizing plate 10 to forma polarizing plate 15 with a pressure-sensitive adhesive. Then, the reverse surface of the pressure-sensitive adhesive sheet 20 to the retardation film 7 is stuck to an image display element 30 to form an optical laminated body 40.

In these examples, the first protection film 4 and the second protection film 3 are generally composed of triacetyl cellulose film or polycycloolefin film, and may be also composed of various kinds of transparent resin films described above. Also, the surface-treated layer formed on the surface of the first protection film 4 may be a hard coat layer, an antiglare layer, an anti-reflection layer and an antistatic layer. Among them, a plurality of layers may be also placed.

As the example shown in FIG. 2, in the case of laminating the retardation film 7 in the polarizing plate 10, an appropriate example of this retardation film 7 in a medium or small-sized liquid crystal display device includes a quarter wavelength plate. In this case, the absorption axis of the polarizing plate 1 and the slow axis of the retardation film 7 as a quarter wavelength plate are generally disposed so as to cross at an angle of approximately 45 degrees, but the angle may be occasionally shifted from 45 degrees to some extent in accordance with the characteristics of the image display element 30. On the other hand, in the case of a large-sized liquid crystal display device such as a television, retardation films having various kinds of retardation values are used in accordance with the characteristics of the image display element 30 for the purpose of retardation compensation and viewing angle compensation of the image display element 30. In this case, the absorption axis of the polarizing plate 1 and the slow axis of the retardation film 7 are generally disposed so as to have an approximately orthogonal or approximately parallel relationship. When the retardation film 7 is composed of a quarter wavelength plate, a uniaxially or biaxially stretched film is appropriately used. Also, when the retardation film 7 is placed for the purpose of retardation compensation and viewing angle compensation of the image display element 30, optical compensation films, such as a film oriented in the thickness direction in addition to uniaxial or biaxial stretching and a film subject to oriented immobilization while applying a retardation development substance such as liquid crystal on a support film, may be used as the retardation film 7, in addition to a uniaxially or biaxially stretched film.

Similarly, as the example shown in FIG. 2, when the retardation film 7 is stuck to the polarizing plate 1 during the formation of the polarizing plate 10 with the interlayer pressure-sensitive adhesive 6 interposed therebetween, a general acrylic pressure-sensitive adhesive is ordinarily used for the interlayer pressure-sensitive adhesive 6, and a pressure-sensitive adhesive sheet as one of polymer films prescribed in the present invention can be also used. As the large-sized liquid crystal display device described above, when the absorption axis of the polarizing plate 1 and the slow axis of the retardation film 7 are disposed so as to have an approximately orthogonal or approximately parallel relationship, roll-to-roll sticking may be used for sticking the polarizing plate 1 and the retardation film 7 with the interlayer pressure-sensitive adhesive 6 interposed therebetween in producing the polarizing plate 10.

The retardation film with the pressure-sensitive adhesive, in which the pressure-sensitive adhesive sheet is formed on the retardation film, may be made into an optical laminated body by sticking the pressure-sensitive adhesive sheet to the image display element, and the polarizing plate may be also stuck on the side of the retardation film.

Here, the polarizing plate is an optical film having the function of emitting polarized light against incident light such as natural light. The polarizing plate includes a linearly polarizing plate having the property of absorbing linearly polarized light having a vibrating surface in a direction, which enters a polarizing plate surface, and transmitting linearly polarized light having a vibrating surface orthogonal thereto; a polarization splitting film having the property of reflecting linearly polarized light having a vibrating surface in a direction, which enters a film surface, and transmitting linearly polarized light having a vibrating surface orthogonal thereto; and an elliptically polarizing plate in which the polarizing plate and the retardation film described later are laminated. Appropriate specific examples of the polarizing plate, particularly, the linearly polarizing plate (may also be occasionally referred to as a polarizer or a polarizer film) include a polarizing plate such that a dichromatic coloring matter such as iodine or dichromatic dye is adsorbed and oriented in an uniaxially stretched polyvinyl alcohol resin film.

The retardation film is an optical film exhibiting optical anisotropy, and examples thereof include stretched films obtained by stretching a polymer film composed of a polymer by approximately from 1.01 to 6 times, such as polyvinyl alcohol, polycarbonate, polyester, polyarylate, polymethacrylate, polyimide, polyolefin, polycycloolefin (norbornene and tetracyclododecene or polymers of derivatives thereof), polystyrene, polysulfone, polyether sulfone, polyvinylidene fluoride/polymethyl methacrylate, liquid crystal polyester, acetyl cellulose, ethylene-vinyl acetate copolymer saponified product, and polyvinyl chloride. Especially, a polymer film obtained by uniaxially or biaxially stretching a polycarbonate film or a polycycloolefin film is preferable. In an embodiment of the present invention, the polymer composition containing the compound (I) and the polymer is made into a film, which is uniaxially or biaxially stretched to obtain the retardation film. Also, a film developing optical anisotropy by application and orientation of a liquid crystal compound can be also used as the retardation film.

The optical film to which a protection film is stuck can be also used as an optical film. A transparent resin film is used as a protection film, and examples of the transparent resin include acetyl cellulose resins typified by triacetyl cellulose and diacetyl cellulose, methacrylic resins typified by polymethyl methacrylate, polyester resins, polyolefin resins, polycarbonate resins, polyether ether ketone resins and polysulfone resins. An ultraviolet absorbing agent such as a salicylate compound, a benzophenone compound, a benzotriazole compound, a triazine compound, a cyanoacrylate compound or a nickel complex salt compound may be blended with a resin constituting the protection film, and in this case, a display device may be appropriately restrained from deteriorating by a synergistic effect with the effect of the light absorptive compound of the present invention. An acetyl cellulose resin film such as a triacetyl cellulose film is appropriately used as the protection film.

Among the optical films described above, the linearly polarizing plate is frequently used in a state such that the protection film is stuck on one surface or both surfaces of a polarizer constituting the linearly polarizing plate, for example, the polarizing plate composed of polyvinyl alcohol resin. Also, the elliptically polarizing plate described above is obtained by laminating the linearly polarizing plate and the retardation film, and the polarizing plate is frequently used in a state such that the protection film is stuck on one surface or both surfaces of the polarizing plate.

The protection film is used for the purpose of protecting the surface of the optical film as a body to be protected from flaws and dirt. Examples of a base material for the protection film include polyolefins such as polyethylene, polypropylene and polymethylpentene; fluorinated polyolefins such as polyvinyl fluoride, polyvinylidene fluoride and polyethylene fluoride; polyesters such as polyethylene naphthalate, polyethylene terephthalate, polybutylene terephthalate and polyethylene terephthalate/isophthalate copolymer; polyamides such as nylon 6 and nylon 6.6; vinyl polymers such as polyvinyl chloride, vinyl chloride-vinyl acetate copolymer, ethylene-vinyl acetate copolymer, ethylene-vinyl alcohol copolymer, polyvinyl alcohol and vinylon; cellulose polymers such as cellulose triacetate, cellulose diacetate, cellophane and triacetyl cellulose; acrylic polymers such as polymethyl methacrylate, polyethyl methacrylate, polyethyl acrylate and polybutyl acrylate; polystyrene, polycarbonate, polyarylate, polyimide and polyurethane.

The pressure-sensitive adhesive sheet includes a pressure-sensitive adhesive. The pressure-sensitive adhesive is an agent for joining polymer films such as the optical film and the protection film to another member. A polymer constituting the pressure-sensitive adhesive is not particularly limited, and examples thereof include poly(meth)acrylate, silicone polymer, polyurethane and rubber. The polymer may be used singly or in combination. Among these, poly(meth) acrylate is appropriately adopted as the polymer in that the selection of kinds of monomers introduced into the polymer allows functionality easily to the pressure-sensitive adhesive.

The thickness of the pressure-sensitive adhesive sheet is not particularly limited, but is ordinarily preferably 30 μm or less, preferably 10 μm or more, more preferably from 10 to 20 μm. When the thickness of the pressure-sensitive adhesive sheet is 30 μm or less, adhesiveness under high temperature and high humidity is improved to bring a tendency to decrease a possibility that lifting and peeling are caused between a glass substrate (an image display element) and the pressure-sensitive adhesive sheet, and a tendency to improve reworkability. When the thickness thereof is 10 μm or more, the pressure-sensitive adhesive sheet varies with the dimensional change even though the dimensions of the optical film stuck thereto change, so as to offer no difference between brightness of the circumferential part and brightness of the central portion in a liquid crystal cell (an image display element) and to bring a tendency to restrain colorless spot and color shading.

The polymer contained in the polymer composition is preferably at least one kind selected from the group consisting of poly(meth)acrylate, polyurethane, polyester, polycarbonate, polycycloolefin and triacetyl cellulose as described above from the viewpoint of being capable of appropriately producing a member constituting an optical laminated body.

The polymer composition contains the compound (I) in an amount of preferably 0.001 to 5 parts by mass (for example, 0.001 to 4 parts by mass), more preferably 0.2 to 4 parts by mass (for example, 0.2 to 3 parts by mass), furthermore preferably 0.3 to 3 parts by mass (for example, 0.3 to 2 parts by mass) with respect to 100 parts by mass of the polymer (solid content). When the content of the compound (I) is equal to or more than the lower limit value, light quantity to be absorbed increases, and the high blue light cutting function can be developed, and a member constituting an optical laminated body (for example, an optical film such as a retardation film, and an image display element such as an organic EL element) may be restrained from deteriorating due to short-wavelength visible light. Also, when the content of the compound (I) is equal to or lower than the upper limit value, the function of pressure sensitive adhesion can be sufficiently exhibited in the case of using the polymer composition for a pressure-sensitive adhesive, and the optical function as an optical film or a protection film obtained by using the polymer composition is hindered with difficulty. Incidentally, the compound (I) is so high in light absorbency as to allow the polymer composition with high light absorbency even though the content of the compound (I) in the polymer composition is low. The content of the compound (I) is so low that the function of pressure sensitive adhesion as a pressure-sensitive adhesive and the optical function as an optical film can be hindered with difficulty.

In a preferable embodiment of the present invention, the polymer is poly(meth)acrylate (A) having as a constitutional unit a (meth)acrylate monomer (A-1) represented by the following formula (A-1):

[Chemical Formula 9]

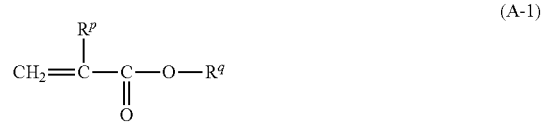

(A-1)

and a (meth)acrylic monomer (A-2) having a hydroxyl group.

In the formula (A-1), $R^p$ denotes a hydrogen atom or a methyl group. Also, $R^q$ denotes an alkyl group or an aralkyl group with a carbon number of preferably 1 to 20, more preferably 1 to 10, in which a hydrogen atom constituting the alkyl group or the aralkyl group is optionally substituted with —O—$(C_2H_4O)_n$—$R^r$, and n denotes an integer of preferably 0 to 4, more preferably 0 to 3, and $R^r$ denotes an alkyl group with a carbon number of preferably 1 to 12, more preferably 1 to 8, or an aryl group with a carbon number of preferably 1 to 12, more preferably 1 to 8.

Specific examples of the (meth)acrylate monomer (A-1) represented by the formula (A-1) include linear acrylic alkyl esters such as methyl acrylate, ethyl acrylate, propyl acrylate, n-butylacrylate, n-octyl acrylate and lauryl acrylate; branched acrylic alkyl esters such as isobutyl acrylate, 2-ethylhexyl acrylate and isooctyl acrylate; linear methacrylic alkyl esters such as methyl methacrylate, ethyl methacrylate, propyl methacrylate, n-butyl methacrylate, n-octyl methacrylate and lauryl methacrylate; branched methacrylic alkyl esters such as isobutyl methacrylate, 2-ethylhexyl methacrylate and isooctyl methacrylate; acrylic ester having an aromatic group such as acrylic phenyl ester and acrylic benzyl ester; and methacrylic esters having an aromatic group such as methacrylic phenyl ester and methacrylic benzyl ester.

The (meth)acrylic monomer (A-2) having a hydroxyl group has at least one hydroxyl group. The (meth)acrylic-monomer (A-2) having a hydroxyl group is preferably represented by the following formula (A-2):

[Chemical Formula 10]

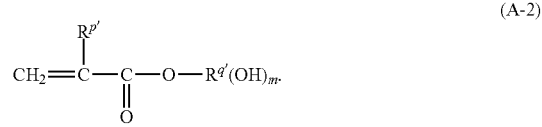

(A-2)

In the formula (A-2), $R^{p'}$ denotes a hydrogen atom or a methyl group. $R^{q'}$ is an alkyl group or an aralkyl group with a carbon number of preferably 1 to 20, more preferably 1 to 10, in which m pieces of hydrogen atoms constituting the alkyl group or the aralkyl group are substituted with an OH group. Incidentally, the hydrogen atom constituting the alkyl group or the aralkyl group is optionally substituted with —O—$(C_2H_4O)_{n'}$—$R^{r'}$, and n' denotes an integer of preferably 0 to 4, more preferably 0 to 3, and $R^{r'}$ denotes an alkyl group with a carbon number of preferably 1 to 12, more preferably 1 to 8, or an aryl group with a carbon number of preferably 1 to 12, more preferably 1 to 8. m denotes an integer of preferably 1 to 10, more preferably 1 to 6, furthermore preferably 1 to 4, particularly 1 to 2, for example, 1.

Specific examples of the (meth)acrylic monomer (A-2) having a hydroxyl group include 2-hydroxyethyl (meth)acrylate, 2-hydroxypropyl (meth)acrylate, 2- or 3-chloro-2-hydroxypropyl (meth)acrylate and diethylene glycol mono (meth)acrylate.

The poly(meth)acrylate (A) contains a constitutional unit derived from the monomer (A-1) in an amount of ordinarily 60 to 99.9% by mass, preferably 80 to 99.6% by mass, and a constitutional unit derived from the monomer (A-2) having a hydroxyl group in an amount of ordinarily 0.1 to 40% by mass, preferably 0.4 to 20% by mass, more preferably 0.5 to 10% by mass, based on the whole solid content.

The polymer having the monomers (A-1) and (A-2) as a constitutional unit may contain another monomer (hereinafter, also referred to as 'monomer (A-3)') as a constitutional unit. Examples of the monomer (A-3) include monomers having a polar functional group other than the monomer (A-2). Examples of the monomer having a polar functional group other than the monomer (A-2) include monomers having a free carboxyl group such as acrylic acid, methacrylic acid and β-carboxyethyl acrylate; monomers having a heterocyclic group such as acryloyl morpholine, vinyl caprolactam, N-vinyl-2-pyrrolidone, tetrahydrofurfuryl (meth)acrylate, caprolactone-modified tetrahydrofurfuryl acrylate, 3,4-epoxycyclohexylmethyl (meth)acrylate, glycidyl (meth)acrylate and 2,5-dihydrofuran; and monomers having an amino group different from a heterocyclic group such as N,N-dimethylaminoethyl (meth)acrylate. These monomers (A-3) may be used singly or in plural different monomers.

The poly(meth)acrylate (A) may contain a constitutional unit derived from the monomer (A-3) in an amount of ordinarily 0.1 to 50% by mass, preferably 0.1 to 20% by mass, more preferably 0.1 to 10% by mass, based on the whole solid content.

The poly(meth)acrylate (A) used for the present invention may contain a monomer as a constitutional unit other than the monomers (A-1), (A-2) and (A-3) described above. Examples thereof include a (meth)acrylate having an alicyclic structure in a molecule, a styrene monomer, a vinyl monomer, a monomer having a plurality of (meth)acryloyl groups in a molecule, and a (meth)acrylamide derivative.

An alicyclic structure is a cycloparaffin structure with a carbon number of ordinarily 5 or more, preferably approximately 5 to 7. Specific examples of the acrylate having an alicyclic structure include isobornyl acrylate, cyclohexyl acrylate, dicyclopentanyl acrylate, cyclododecyl acrylate, methylcyclohexyl acrylate, trimethylcyclohexyl acrylate, tert-butylcyclohexyl acrylate, cyclohexyl α-ethoxyacrylate and cyclohexylphenyl acrylate, and specific examples of the methacrylate having an alicyclic structure include isobornyl methacrylate, cyclohexyl methacrylate, dicyclopentanyl methacrylate, cyclododecyl methacrylate, methylcyclohexyl methacrylate, trimethylcyclohexyl methacrylate, tert-butylcyclohexyl methacrylate and cyclohexylphenyl methacrylate.

Examples of the styrene monomer include styrene as well as alkyl styrenes such as methyl styrene, dimethyl styrene, trimethyl styrene, ethyl styrene, diethyl styrene, triethyl styrene, propyl styrene, butyl styrene, hexyl styrene, heptyl styrene and octyl styrene; halogenated styrenes such as fluorostyrene, chlorostyrene, bromostyrene, dibromostyrene and iodostyrene; nitrostyrene, acetylstyrene, methoxystyrene, and divinylbenzene.

Examples of the vinyl monomer include fatty acid vinyl esters such as vinyl acetate, vinyl propionate, vinyl butyrate, vinyl 2-ethylhexoate and vinyl laurate; halogenated vinyls such as vinyl chloride and vinyl bromide; halogenated vinylidenes such as vinylidene chloride; nitrogen-containing aromatic vinyls such as vinylpyridine, vinylpyrrolidone and vinylcarbazole; conjugate diene monomers such as butadiene, isoprene and chloroprene; and acrylonitrile and methacrylonitrile.

Examples of the monomer having a plurality of (meth)acryloyl groups in a molecule include monomers having two (meth)acryloyl groups in a molecule such as 1,4-butanediol di(meth)acrylate, 1,6-hexanediol di(meth)acrylate, 1,9-nonanediol di(meth)acrylate, ethylene glycol di(meth)acrylate, diethylene glycol di(meth)acrylate, tetraethylene glycol di(meth)acrylate and tripropylene glycol di(meth)acrylate; and monomers having three (meth)acryloyl groups in a molecule such as trimethylolpropane tri(meth)acrylate.

Examples of the (meth)acrylamide derivative include N-methylol(meth)acrylamide, 2-hydroxyethyl(meth)acrylamide, 3-hydroxypropyl(meth)acrylamide, 4-hydroxybutyl (meth)acrylamide, 5-hydroxypentyl(meth)acrylamide, 6-hydroxyhexyl(meth)acrylamide, N-methoxymethyl(meth)acrylamide, N-ethoxymethyl(meth)acrylamide, N-propoxymethyl(meth)acrylamide, N-butoxymethyl(meth)acrylamide, N,N-dimethyl(meth)acrylamide, N,N-diethyl (meth)acrylamide, N-isopropyl(meth)acrylamide, N-dimethylaminopropyl(meth)acrylamide, N-(1,1-dimethyl-3-oxobutyl)(meth)acrylamide, N-[2-(2-oxo-1-imidazolidinyl) ethyl](meth)acrylamide and 2-acryloylamino-2-methyl-1-propanesulfonic acid.

The monomer other than the monomers (A-1), (A-2) and (A-3) can be used singly or in combination of two or more kinds thereof. A constitutional unit derived from the monomer other than the monomers (A-1), (A-2) and (A-3) is contained in the poly(meth)acrylate (A) used for a pressure-sensitive adhesive in an amount of ordinarily 0 to 20% by mass, preferably 0 to 10% by mass, based on the whole solid content of (A). Incidentally, the total of constitutional units derived from the monomers contained in the poly(meth)acrylate (A) is 100% by mass.

The polymer composition according to an embodiment of the present invention may contain the poly(meth)acrylate (A) in one kind or in two or more kinds.

With regard to the poly(meth)acrylate (A), a weight-average molecular weight ($M_w$) in terms of standard polystyrene by gel permeation chromatography (GPC) is preferably from 500000 to 2000000, more preferably from 550000 to 1800000, furthermore preferably from 600000 to 1500000. When the weight-average molecular weight in terms of standard polystyrene is equal to or more than the lower limit value, adhesiveness under high temperature and high humidity is improved to bring a tendency to decrease a possibility that lifting and peeling are caused between a glass substrate (an image display element) and the pressure-sensitive adhesive sheet, and a tendency to improve reworkability. When this weight-average molecular weight is equal to or lower than the upper limit value, in the case of sticking the pressure-sensitive adhesive sheet to an optical film, the pressure-sensitive adhesive sheet varies with the dimensional change even though the dimensions of the optical film stuck thereto change, so as to offer no difference between brightness of the circumferential part and brightness of the central portion in a liquid crystal cell (an image display element) and to bring a tendency to restrain colorless spot and color shading. The molecular-weight distribution represented by a ratio ($M_w/M_n$) between weight-average molecular weight ($M_w$) and number-average molecular weight ($M_n$) is within a range of ordinarily approximately 2 to 10.

The poly(meth)acrylate (A) may be composed of only the poly(meth)acrylate described above with comparatively high molecular weight, and may be composed of a mixture of the poly(meth)acrylate (A) and poly(meth)acrylate different therefrom. Examples of the poly(meth)acrylate usable by mixture include poly(meth)acrylates having a constitutional unit derived from (meth)acrylate as the main component (for example, polymethyl (meth)acrylate), in which a weight-average molecular weight is within a range of 50000 to 300000.

A solution obtained by dissolving the poly(meth)acrylate contained in the polymer composition (in the case of combining two or more kinds of poly(meth)acrylate, a mixture thereof) in ethyl acetate to adjust to a solid content concentration of 20% by mass preferably exhibits a viscosity of 20 Pa·s or less, and further preferably 0.1 to 7 Pa·s at 25° C. When the viscosity is 20 Pa·s or less, adhesiveness under high temperature and high humidity is improved to bring a tendency to decrease a possibility that lifting and peeling are caused between an image display element and the pressure-sensitive adhesive sheet, and a tendency to improve reworkability. The viscosity can be measured by a Brookfield viscometer.

The poly(meth)acrylate can be produced by various known methods such as a solution polymerization method, an emulsion polymerization method, a block polymerization method and a suspension polymerization method. A polymerization initiator is ordinarily used in producing this poly(meth)acrylate. The polymerization initiator is used by approximately from 0.001 to 5 parts by mass with respect to 100 parts by mass of the total of all monomers used for producing the poly(meth)acrylate.

A thermal polymerization initiator and a photo polymerization initiator are used as the polymerization initiator. Examples of the photo polymerization initiator include 4-(2-hydroxyethoxy)phenyl(2-hydroxy-2-propyl)ketone. Examples of the thermal polymerization initiator include azo compounds such as 2,2'-azobisisobutyronitrile, 2,2'-azobis(2-methylbutyronitrile), 1,1'-azobis(cyclohexane-1-carbonitrile), 2,2'-azobis(2,4-dimethylvaleronitrile), 2,2'-azobis(2,4-dimethyl-4-methoxyvaleronitrile), dimethyl-2,2'-azobis(2-methylpropionate) and 2,2'-azobis(2-hydroxymethylpropionitrile); organic peroxides such as lauryl peroxide, tert-butylhydroperoxide, benzoyl peroxide, tert-butylperoxybenzoate, cumene hydroperoxide, diisopropylperoxycarbonate, dipropylperoxydicarbonate, tert-butylperoxyneodecanoate, tert-butylperoxypivalate and (3,5,5-trimethylhexanoyl)peroxide; and inorganic peroxides such as potassium persulfate, ammonium persulfate and hydrogen peroxide. Also, a redox initiator including a peroxide and a reducing agent together can be used as the polymerization initiator.

A solution polymerization method among the methods described above is preferable as a method for producing the poly(meth)acrylate. Specific examples of the solution polymerization method include a method such that a desired monomer and an organic solvent are mixed, and a thermal polymerization initiator is added thereto under a nitrogen atmosphere and the mixture is stirred at approximately from 40 to 90° C., preferably approximately from 60 to 80° C. for approximately from 3 to 10 hours. In order to control the reaction, a monomer and a thermal polymerization initiator may be added during the polymerization continuously or intermittently, or added while dissolved in an organic solvent. Here, examples of the organic solvent to be used include aromatic hydrocarbons such as toluene and xylene; esters such as ethyl acetate and butyl acetate; aliphatic alcohols such as propyl alcohol and isopropyl alcohol; and ketones such as acetone, 2-butanone and methyl isobutyl ketone.

In an embodiment of the present invention, the polymer composition may contain a crosslinking agent as required in addition to the polymer and the compound (I). The crosslinking agent is a compound to react with particularly a hydroxyl group or a constitutional unit derived from a polar functional group-containing monomer in the poly(meth)acrylate (A), so that the poly(meth)acrylate (A) is crosslinked. Specific examples thereof include an isocyanate compound, an epoxy compound, an aziridine compound and a metal chelate compound. Among these, an isocyanate compound, an epoxy compound and an aziridine compound have at least two functional groups in a molecule, which can be reacted with a hydroxyl group and occasionally a polar functional group in the poly(meth)acrylate (A).

The isocyanate compound is a compound having at least two isocyanato groups (—NCO) in a molecule, and examples thereof include tolylene diisocyanate, hexamethylene diisocyanate, isophorone diisocyanate, xylylene diisocyanate, hydrogenated xylylene diisocyanate, diphenylmethane diisocyanate, hydrogenated diphenylmethane diisocyanate, naphthalene diisocyanate and triphenylmethane triisocyanate. An adduct in which these isocyanate compounds are reacted with polyols such as glycerol and trimethylolpropane, and a dimer and a trimer of the isocyanate compounds may be made into the crosslinking agent used for a pressure-sensitive adhesive. Two or more kinds of the isocyanate compounds can be mixed and used.

The epoxy compound is a compound having at least two epoxy groups in a molecule, and examples thereof include bisphenol A type epoxy resin, ethylene glycol diglycidyl ether, polyethylene glycol diglycidyl ether, glycerol diglycidyl ether, glycerol triglycidyl ether, 1,6-hexanediol diglycidyl ether, trimethylolpropane triglycidyl ether, N,N-diglycidyl aniline, N,N,N',N'-tetraglycidyl-m-xylenediamine and 1,3-bis(N,N'-diglycidylaminomethyl)cyclohexane. Two or more kinds of the epoxy compounds can be mixed and used.

The aziridine compound is a compound having at least two three-membered ring skeletons composed of one nitrogen atom and two carbon atoms, which is also called ethyleneimine, in a molecule, and examples thereof include diphenylmethane-4,4'-bis(1-aziridinecarboxamide), toluene-2,4-bis(1-aziridinecarboxamide), triethylenemelamine, isophthaloylbis-1-(2-methylaziridine), tris-1-aziridinylphosphine oxide, hexamethylene-1,6-bis(1-aziridinecarboxamide), trimethylolpropane-tri-β-aziridinyl propionate and tetramethylolmethane-tri-β-aziridinyl propionate.

Examples of the metal chelate compound include compounds in which acetylacetone and ethyl acetoacetate are coordinated with polyvalent metals such as aluminum, iron, copper, zinc, tin, titanium, nickel, antimony, magnesium, vanadium, chromium and zirconium.

Among these crosslinking agents, the isocyanate compound, especially, xylylene diisocyanate, tolylene diisocyanate, hexamethylene diisocyanate, an adduct in which these isocyanate compounds are reacted with polyols such as glycerol and trimethylolpropane, a mixture of a dimer and a trimer of the isocyanate compounds, and a mixture of these isocyanate compounds are preferably used. Appropriate examples of the isocyanate compound include tolylene diisocyanate, an adduct in which tolylene diisocyanate is reacted with a polyol, a dimer of tolylene diisocyanate and a trimer of tolylene diisocyanate, hexamethylene diisocyanate, an adduct in which hexamethylene diisocyanate is reacted with a polyol, a dimer of hexamethylene diisocyanate, and a trimer of hexamethylene diisocyanate.

The polymer composition contains preferably from 0.01 to 5 parts by mass, more preferably from 0.05 to 2 parts by mass, furthermore preferably from 0.1 to 1 part by mass of a crosslinking agent with respect to 100 parts by mass of the polymer (solid content). When the content of the crosslinking agent is equal to or more than the lower limit value, durability of the pressure-sensitive adhesive sheet obtained from the polymer composition tends to be improved; and when the content of the crosslinking agent is equal to or lower than the upper limit value, colorless spot in applying a polymer film obtained from the polymer composition to a liquid crystal display device becomes inconspicuous.

When the polymer composition contains the poly(meth)acrylate (A), the polymer composition can be appropriately used as a pressure-sensitive adhesive. The compound (I) hinders the pressure-sensitive adhesion function with difficulty, and the polymer composition can exhibit high pressure-sensitive adhesion function as a pressure-sensitive adhesive, and the compound (I) is so excellent in light-selective absorbency in a specific range as to allow a pressure-sensitive adhesive excellent in both pressure-sensitive adhesion function and light-selective absorbency. In addition, the compound (I) is excellent in affinity with the poly(meth)acrylate so that a bleed out of the compound (I) is caused with difficulty to allow stable light absorbency to be exhibited. The pressure-sensitive adhesive sheet may be obtained from such a pressure-sensitive adhesive.

A silane compound is preferably contained in the polymer composition, and especially, a silane compound is preferably contained in the polymer before blending the crosslinking agent. The silane compound improves adhesive strength to glass, so that the inclusion of the silane compound allows adhesive strength as the pressure-sensitive adhesive sheet to be improved and allows peeling and lifting to be caused with difficulty in a base material applied to the pressure-sensitive adhesive sheet.

The blended amount of the silane compound in the polymer composition is ordinarily approximately from 0.01 to 10 parts by mass, preferably from 0.05 to 5 parts by mass with respect to 100 parts by mass of the polymer (solid content) (in the case of using two or more kinds of silane compound, a mixture thereof). When the content of the silane compound is equal to or more than the lower limit value, the adhesion properties of the polymer composition are improved. When the content of the silane compound is equal to or lower than the upper limit value, a bleed out of the silane compound from the polymer composition tends to be restrained.

The polymer composition may further contain a crosslinking catalyst, an antistatic agent, a weathering stabilizer, a tackifier, a plasticizer, a softening agent, a dye, a pigment, an inorganic filler and resins other than an acrylic resin. In the case of forming the pressure-sensitive adhesive sheet by using the polymer composition, it is useful that an ultraviolet-curing compound is blended with the polymer composition, the mixture is applied on a base material and then irradiated with ultraviolet rays to be cured so that the harder pressure-sensitive adhesive sheet is obtained. Especially, when the crosslinking agent and a crosslinking catalyst are blended with the polymer composition, the pressure-sensitive adhesive sheet can be prepared in a short-time aging, and lifting and peeling may be restrained from occurring between the pressure-sensitive adhesive sheet and the base material, and foaming may be restrained from occurring in the pressure-sensitive adhesive sheet, and reworkability may be occasionally improved. Examples of the crosslinking catalyst include amine compounds such as hexamethylenediamine, ethylenediamine, polyethyleneimine, hexamethylenetetramine, diethylenetriamine, triethylenetetramine, isophoronediamine, trimethylenediamine, polyamino resins and melamine resins. When the amine compound as the crosslinking catalyst is blended with the polymer composition, the isocyanate compound is preferable as the crosslinking agent.

Each of the components constituting the polymer composition may constitute the polymer composition in a state of being dissolved in a solvent. Examples of the solvent include alcohol solvents such as methanol, ethanol, ethylene glycol, isopropyl alcohol, propylene glycol, methylcellosolve, butylcellosolve and propylene glycol monomethyl ether; ester solvents such as ethyl acetate, butyl acetate, ethylene glycol methyl ether acetate, γ-butyrolactone, propylene glycol monomethyl ether acetate and ethyl lactate; ketone solvents such as acetone, 2-butanone, cyclopentanone, cyclohexanone, methyl amyl ketone and methyl isobutyl ketone; aliphatic hydrocarbon solvents such as pentane, hexane and heptane; aromatic hydrocarbon solvents such as toluene and xylene; nitrile solvents such as acetonitrile; ether solvents such as tetrahydrofuran and dimethoxyethane; and chlorinated hydrocarbon solvents such as chloroform and chlorobenzene. Especially, 2-butanone, ethyl acetate and toluene are preferable from the viewpoint of solubility and temporal stability of the polymer composition and residual solvent amount control in the drying process in producing a film.

The polymer film preferably satisfies the following formula (d).

$$A(420)/A(400) \leq 0.4 \qquad (d)$$

In the formula (d), A(400) denotes absorbance at a wavelength of 400 nm and A(420) denotes absorbance at a wavelength of 420 nm. The value of A(420)/A(400) expresses the intensity of absorption at a wavelength of 400 nm to the intensity of absorption at a wavelength of 420 nm, and the smaller value shows more peculiar absorption in a wavelength region around 400 nm as compared with absorption in a wavelength region around 420 nm. The smaller value offers a transparent polymer film with less yellowness.

When the polymer film satisfies the formula (d), light with a wavelength of 420 nm is absorbed with difficulty and also blue visible light is absorbed with difficulty while light with a wavelength of 400 nm is absorbed, so that the polymer film having the blue light cutting function and hindering favorable color presentation with difficulty is obtained. In the case of incorporating the polymer film into an optical laminated body, a member constituting an optical laminated body (for example, an optical film such as a retardation film, and display elements such as an organic EL element and a liquid crystal display element) can be restrained from deteriorating in performance due to short-wavelength visible light (that is, light around a wavelength of 400 nm). The value of A(420)/A(400) in the polymer film is preferably 0.4 or less, more preferably 0.3 or less, furthermore preferably 0.25 or less, particularly preferably 0.2 or less, especially preferably 0.15 or less, for example, 0.1 or less. The lower limit value thereof is not particularly limited but preferably ordinarily 0.01 or more from the viewpoint of maintaining absorptivity around 400 nm in the polymer film. In an appropriate embodiment of the present invention, the value of A(420)/A(400) is from 0.05 to 0.15.

Also, the polymer film of the present invention preferably satisfies the following formula (e).

$$A(400) \geq 0.5 \qquad (e)$$

The larger value of A(400) indicates higher absorption at a wavelength of 400 nm, and when this value is less than 0.5, the absorption at a wavelength of 400 nm is so weak as to secure sufficiently high light resistance to short-wavelength visible light around 400 nm with difficulty. Accordingly, the value of A(400) in the polymer film of the present invention is preferably 0.8 or more, more preferably 1 or more, furthermore preferably 1.2 or more, particularly preferably 1.5 or more, especially preferably 1.8 or more, for example, 2 or more. The upper limit value of A(400) is not particularly limited but preferably ordinarily 5 or less from the viewpoint of avoiding a bleed out of the compound (I) in the polymer film.

Another embodiment of the present invention can also provide a photopolymerizable composition (hereinafter, also referred to as 'a photopolymerizable composition of the present invention') containing a monomer (B) having a photopolymerizable functional group, a photopolymerization initiator (C), a solvent (D) and the compound (I). Also, a cured layer can be provided by applying the photopolymerizable composition of the present invention on a base material to cause a curing reaction. The cured layer can be used as a protection film, an over coat layer or a separator film.

The photopolymerizable composition of the present invention contains the compound (I) in an amount of preferably 0.005 to 0.5 parts by mass, more preferably 0.007 to 0.3 parts by mass, furthermore preferably 0.008 to 0.2 parts by mass, for example, 0.01 to 0.1 parts by mass with respect to the monomer (B) having a photopolymerizable functional group. When the content of the compound (I) is equal to or more than the lower limit value, light quantity to be absorbed increases, and the high blue light cutting function can be developed, and the cured layer itself can be restrained from deteriorating due to short-wavelength visible light, and other members can be restrained from deteriorating. When the content of the compound (I) is equal to or lower than the upper limit value, a favorable cured layer can be obtained without hindering the monomer (B) having a photopolymerizable functional group from being cured while causing a bleed out of the compound (I) with difficulty in the cured layer composed of a polymer of the photopolymerizable composition. Incidentally, the compound (I) is so high in light absorbency as to allow the photopolymerizable composition with high light absorbency even though the content of the compound (I) in the photopolymerizable composition is low. The content of the compound (I) is so low that the optical function as a protection film can be hindered with difficulty.

A photopolymerizable functional group of the monomer (B) having a photopolymerizable functional group refers to a group capable of involving a polymerization reaction by an active radical and acid generated from a photopolymerization initiator. Examples of the photopolymerizable functional group include a vinyl group, a vinyloxy group, a 1-chlorovinyl group, an isopropenyl group, a 4-vinylphenyl group, an acryloyloxy group, a methacryloyloxy group, an oxiranyl group and an oxetanyl group. Especially, an acryloyloxy group, a methacryloyloxy group, a vinyloxy group, an oxiranyl group and an oxetanyl group are preferable, and an acryloyloxy group is more preferable.

Specific examples of the monomer (B) include a polyester (meth)acrylate monomer, a monofunctional (meth)acrylate monomer, a polyfunctional (meth)acrylate monomer, a urethane (meth)acrylate monomer and an epoxy(meth)acrylate monomer.

The monofunctional acrylate is a compound having a group (hereinafter, may be referred to as a (meth)acryloyloxy group) selected from the group consisting of an acryloyloxy group ($CH_2$=CH—COO—) and a methacryloyloxy group ($CH_2$=C($CH_3$)—COO—). Also, (meth)acrylate means acrylate or methacrylate.

Examples of the monofunctional acrylate having a (meth)acryloyloxy group include alkyl (meth)acrylate with a carbon number of 4 to 16, β-carboxyalkyl (meth)acrylate with a carbon number of 2 to 14, alkylated phenyl (meth)acrylate with a carbon number of 2 to 14, methoxypolyethylene glycol (meth)acrylate, phenoxypolyethylene glycol (meth)acrylate and isobonyl (meth)acrylate.

The polyfunctional (meth)acrylate monomer is a compound having two or more (meth)acryloyloxy groups, and preferably a compound having two to six (meth)acryloyloxy groups.

Examples of the polyfunctional acrylate having two (meth)acryloyloxy groups include 1,3-butanediol di(meth)acrylate; 1,3-butanediol (meth)acrylate; 1,6-hexanediol di(meth)acrylate; ethylene glycol di(meth)acrylate; diethylene glycol di(meth)acrylate; neopentyl glycol di(meth)acrylate; triethylene glycol di(meth)acrylate; tetraethylene glycol di(meth)acrylate; polyethylene glycol diacrylate; bis (acryloyloxyethyl)ether of bisphenol A; ethoxylated bisphenol A di(meth)acrylate; propoxylated neopentyl glycol di(meth)acrylate; ethoxylated neopentyl glycol di(meth)acrylate; and 3-methylpentanediol di(meth)acrylate.

Examples of the polyfunctional acrylate having three to six (meth)acryloyloxy groups include trimethylolpropane tri(meth)acrylate; pentaerythritol tri(meth)acrylate; tris(2-hydroxyethyl)isocyanurate tri(meth)acrylate; ethoxylated trimethylolpropane tri(meth)acrylate; propoxylated trimethylolpropane tri(meth)acrylate; pentaerythritol tetra(meth)acrylate; dipentaerythritol penta(meth)acrylate; dipentaerythritol hexa(meth)acrylate; tripentaerythritol tetra (meth)acrylate; tripentaerythritol penta(meth)acrylate; tripentaerythritol hexa(meth)acrylate; tripentaerythritol hepta(meth)acrylate; tripentaerythritol octa(meth)acrylate; a reactant of pentaerythritol tri(meth)acrylate and acid anhydride; a reactant of dipentaerythritol penta(meth)acrylate and acid anhydride; a reactant of tripentaerythritol hepta (meth)acrylate and acid anhydride;

caprolactone-modified trimethylolpropane tri(meth)acrylate; caprolactone-modified pentaerythritol tri(meth)acrylate; caprolactone-modified tris(2-hydroxyethyl)isocyanurate tri(meth)acrylate; caprolactone-modified pentaerythritol tetra(meth)acrylate; caprolactone-modified dipentaerythritol penta(meth)acrylate; caprolactone-modified dipentaerythritol hexa(meth)acrylate; caprolactone-modified tripentaerythritol tetra(meth)acrylate; caprolactone-modified tripentaerythritol penta(meth)acrylate; caprolactone-modified tripentaerythritol hexa(meth)acrylate; caprolactone-modified tripentaerythritol hepta(meth)acrylate; caprolactone-modified tripentaerythritol octa(meth)acrylate; a reactant of caprolactone-modified pentaerythritol tri(meth)acrylate and acid anhydride; a reactant of caprolactone-modified dipentaerythritol penta(meth)acrylate and acid anhydride; and a reactant of caprolactone-modified tripentaerythritol hepta(meth)acrylate and acid anhydride.

The caprolactone modification means that an open-ring body or open-ring polymer of caprolactone is introduced between an alcohol-derived site of a (meth)acrylate compound and a (meth)acryloyloxy group.

The polyfunctional acrylate is commercially available. Examples of the commercially available articles include A-DOD-N, A-HD-N, A-NOD-N, APG-100, APG-200, APG-400, A-GLY-9E, A-GLY-20E, A-TMM-3, A-TMPT, AD-TMP, ATM-35E, A-TMMT, A-9550, A-DPH, HD-N, NOD-N, NPG, TMPT (manufactured by Shin Nakamura Chemical Co., Ltd.), "ARONIX M-220", "ARONIX M-325", "ARONIX M-240", "ARONIX M-270", "ARONIX M-309", "ARONIX M-310", "ARONIX M-321", "ARONIX M-350", "ARONIX M-360", "ARONIX M-305", "ARONIX M-306", "ARONIX M-450", "ARONIX M-451", "ARONIX M-408", "ARONIX M-400", "ARONIX M-402", "ARONIX M-403", "ARONIX M-404", "ARONIX M-405", "ARONIX M-406" (manufactured by Toagosei Co., Ltd.), "EBECRYL 11", "EBECRYL 145", "EBECRYL 150", "EBECRYL 40", "EBECRYL 140", "EBECRYL 180", DPGDA, HDDA, TPGDA, HPNDA, PETIA, PETRA, TMPTA, TMPEOTA, DPHA, EBECRYL series (manufactured by DAICEL-ALLNEX LTD.).

The polyester (meth)acrylate monomer is sold as the product name of "ARONIX" by Toagosei Co., Ltd. The urethane (meth)acrylate monomer is sold as the product name of "EBECRYL" by DAICEL-ALLNEX LTD.

The monomer (B) may be a monomer of an aliphatic or alicyclic alkyl structure, or a monomer of a structure with an aromaticity, but is preferably a monomer of an aliphatic or alicyclic alkyl structure in the case of obtaining an uncolored cured layer.

The content of the monomer (B) in the photopolymerizable composition is ordinarily from 70 to 99.5 parts by mass, preferably from 80 to 99 parts by mass, more preferably from 90 to 98 parts by mass, furthermore preferably from 93 to 97 parts by mass with respect to 100 parts by mass of the solid content of the photopolymerizable composition from the viewpoint of obtaining a high-strength cured layer. The solid content in the specification refers to the total amount of the components of the photopolymerizable composition except the solvent.

The photopolymerization initiator (C) is a photopolymerization initiator for generating an active radical by the function of light, and is a compound for initiating a polymerization reaction of the monomer (B). Examples of the photopolymerization initiator (C) include benzoin compounds, benzophenone compounds, alkylphenone compounds, acylphosphine oxide compounds, triazine compounds, iodonium salts and sulfonium salts. Specific examples of the photopolymerization initiator (C) include photopolymerization initiators usable for the polymerization of the poly(meth)acrylate. These photopolymerization initiators may be used singly or in combination of two or more kinds thereof.

Commercially available articles may be used for the photopolymerization initiator. Examples of the commercially available polymerization initiator include Irgacure (registered trademark) 907, 184, 651, 819, 250 and 369 (manufactured by BASF JAPAN); SEIKUOL (registered trademark) BZ, Z and BEE (manufactured by Seiko Chemical Co., Ltd.); kayacure (registered trademark) BP100 and UVI-6992 (manufactured by The Dow Chemical Company); ADEKA OPTOMER SP-152 and SP-170 (manufactured by ADEKA CORPORATION); TAZ-A and TAZ-PP (manufactured by Nihon SiberHegner K.K.); and TAZ-104 (manufactured by SANWA CHEMICAL CO., LTD.).

The content of the photopolymerization initiator (C) is ordinarily from 0.1 to 30 parts by mass, preferably from 0.3 to 10 parts by mass, more preferably from 0.4 to 8 parts by mass with respect to 100 parts by mass of the monomer (B) from the viewpoint of allowing a favorable cured layer to be formed from the photopolymerizable composition of the present invention without causing coloration resulting from the photopolymerization initiator, and obtaining a cured layer excellent in light resistance.

The solvent (D) is preferably a solvent capable of completely dissolving the monomer (B) and the compound (I), and preferably an inactive solvent in a polymerization reaction of the monomer (B).

Examples of the solvent (D) include alcohol solvents such as methanol, ethanol, ethylene glycol, isopropyl alcohol, propylene glycol, methylcellosolve, butylcellosolve and propylene glycol monomethyl ether; ester solvents such as ethyl acetate, butyl acetate, ethylene glycol methyl ether acetate, γ-butyrolactone, propylene glycol monomethyl ether, propylene glycol monomethyl ether acetate and ethyl lactate; ketone solvents such as acetone, 2-butanone, cyclopentanone, cyclohexanone, methyl amyl ketone and methyl isobutyl ketone; aliphatic hydrocarbon solvents such as pentane, hexane and heptane; aromatic hydrocarbon solvents such as toluene and xylene; nitrile solvents such as acetonitrile; ether solvents such as tetrahydrofuran and dimethoxyethane; aprotic polar solvents such as N,N'-dimethylformamide, N,N'-dimethylacetamide, N-methyl-2-pyrrolidone and dimethyl sulfoxide; and chlorinated hydrocarbon solvents such as chloroform and chlorobenzene. These solvents may be used singly or in combination of two or more kinds thereof.

The content of the solvent (D) is preferably from 30 to 98% by mass with respect to the total amount of the photopolymerizable composition. In other words, the solid content in the photopolymerizable composition is preferably from 2 to 70% by mass. When the solid content is 70% by mass or less, the viscosity of the photopolymerizable composition is so low that the thickness of a cured layer formed from the composition is approximately uniform to bring a tendency to cause unevenness in the cured layer with difficulty. Also, the solid content can be determined in consideration of the thickness of a cured layer to be produced.

The photopolymerizable composition may contain a sensitizer, a polymerization inhibitor and/or a leveling agent as required, in addition to the monomer (B), the photopolymerization initiator (C) and the solvent (D).

The sensitizer is preferably a photosensitizer. Examples of the sensitizer include xanthone compounds such as xanthone and thioxanthone (for example, 2,4-diethylthioxanthone and 2-isopropylthioxanthone); anthracene compounds such as anthracene and alkoxy group-containing anthracene (for example, dibutoxyanthracene); phenothiazine and rubrene.

The content of the sensitizer in the photopolymerizable composition is ordinarily from 0.1 to 30 parts by mass, preferably from 0.5 to 10 parts by mass, more preferably from 0.5 to 8 parts by mass with respect to 100 parts by mass of the solid content in the photopolymerizable composition.

Examples of the polymerization inhibitor include radical scavengers such as hydroquinone, methoquinone, 3,5-di-tert-butyl-4-hydroxytoluene (BHT), alkoxy group-containing hydroquinone, alkoxy group-containing catechol (such as butylcatechol), pyrogallol and 2,2,6,6-tetramethyl-1-piperidinyloxy radical; thiophenols; β-naphthylamines and β-naphthols.

The content of the polymerization inhibitor in the photopolymerizable composition is ordinarily from 0.1 to 30 parts by mass, preferably from 0.5 to 10 parts by mass, more preferably from 0.5 to 8 parts by mass with respect to 100 parts by mass of the content of the monomer (B).

The leveling agent has the function of adjusting the fluidity of the photopolymerizable composition to further flatten a coating layer of the photopolymerizable composition, and examples thereof include surfactants. Preferable examples of the leveling agent include a leveling agent containing a polyacrylate compound as the main component, a leveling agent containing a fluorine atom-containing compound as the main component, and a silicone-based leveling agent.

Examples of the leveling agent containing a polyacrylate compound as the main component include BYK-350, BYK-352, BYK-353, BYK-354, BYK-355, BYK-358N, BYK-361N, BYK-380, BYK-381 and BYK-392 (manufactured by BYK Chemie).

Examples of the leveling agent containing a fluorine atom-containing compound as the main component include MEGAFAC (registered trademark) R-08, R-30, R-90, F-410, F-411, F-443, F-445, F-470, F-471, F-477, F-479, F-482 and F-483 (manufactured by DIC Corporation); Surflon (registered trademark) S-381, S-382, S-383, S-393, SC-101, SC-105, KH-40 and SA-100 (manufactured by AGC SEIMI CHEMICAL CO., LTD.); E1830 and E5844 (manufactured by Daikin Fine Chemical Laboratory); and EFTOP EF301, EF303, EF351 and EF352 (manufactured by Mitsubishi Materials Electronic Chemicals Co., Ltd.).

Examples of the silicone-based leveling agent include DC3PA, SH7PA, DC11PA, SH28PA, SH29PA, SH30PA, ST80PA, ST86PA, SH8400, SH8700, SF8410 and FZ2123 (all of the above are manufactured by Dow Corning Toray Co., Ltd.), KP-323, KP-326, KP-341, KP-104, KP-110 and KP-112 (all of the above are manufactured by Shin-Etsu Chemical Co., Ltd.), and TSF400, TSF401, TSF410, TSF4300, TSF4440, TSF4445, TSF-4446, TSF4452 and TSF4460 (all of the above are manufactured by Momentive Performance Materials Japan Inc.).

The content of the leveling agent in the photopolymerizable composition is ordinarily 0.01 parts by mass or more and 5 parts by mass or less, preferably 0.05 parts by mass or more and 4 parts by mass or less, more preferably 0.1 parts by mass or more and 3 parts by mass or less with respect to 100 parts by mass of the solid content in the photopolymerizable composition. The content of the leveling agent preferably falls within the range for the reason that the obtained cured layer tends to be further flattened. It is not preferable that the content of the leveling agent in the monomer (B) exceeds the range for the reason that the obtained cured layer tends to be easily uneven. The photopolymerizable composition may contain two or more kinds of the leveling agent.

A cured layer comprising a cured material of the photopolymerizable composition preferably satisfies the following formulae (1) to (3):

$$0 \text{ nm} \leq Re < 10 \text{ nm} \quad (1)$$

$$A(420)/A(400) \leq 0.4 \quad (2)$$

$$Hz \leq 3. \quad (3)$$

In the formula (1), Re denotes an in-plane retardation value at a wavelength of 550 nm. Re is preferably less than 10 nm, more preferably less than 8 nm, furthermore preferably less than 5 nm. When Re is less than the upper limit value, the cured layer is optically uniform and can be utilized as a protection film without deteriorating the display performance of a display.

In the formula (2), A(420) denotes absorbance at 420 nm and A(400) denotes absorbance at 400 nm. A(420)/A(400) is preferably 0.4 or less, more preferably 0.25 or less, furthermore preferably 0.2 or less, especially preferably 0.1 or less, for example, 0.05 or less. When A(420)/A(400) is equal to or lower than the upper limit value, light around 420 nm is absorbed with difficulty whereas light around 400 nm can be selectively absorbed, so that the cured layer having the blue light cutting function and hindering favorable color presentation with difficulty is obtained. In the case of incorporating the cured layer into an optical laminated body, a member constituting an optical laminated body can be restrained from deteriorating in performance due to short-wavelength visible light. Incidentally, the lower limit value of A(420)/A(400) is ordinarily 0.01 or more. In an appropriate embodiment of the present invention, the value of A(420)/A(400) is from 0.02 to 0.15.

In the formula (3), Hz denotes turbidity. Hz is preferably 3 or less, more preferably 2 or less, furthermore preferably 1 or less. When Hz is equal to or lower than the upper limit value, the cured layer is transparent and can be utilized as a protection film without deteriorating the display performance of a display. Incidentally, the lower limit value of Hz is ordinarily 0.01 or more.

Also, the cured layer preferably satisfies the following formula (4):

$$A(400) \geq 0.5. \quad (4)$$

The larger value of A(400) indicates higher absorption at a wavelength of 400 nm, and when this value is less than 0.5, the absorption at a wavelength of 400 nm is so weak as to secure sufficiently high light resistance to short-wavelength visible light around 400 nm with difficulty. Accordingly, the value of A (400) in the cured layer of the present invention is preferably 0.8 or more, more preferably 1 or more, furthermore preferably 1.2 or more, for example, 1.4 or more. The upper limit value of A(400) is not particularly limited, but is preferably ordinarily 5 or less from the viewpoint of avoiding a bleed out of the compound (I) in the cured layer.

In the cured layer, the compound (I) is so excellent in affinity with various compounds as to cause a bleed out of the compound (I) with difficulty and exhibit stable light absorbency.

The thickness of the cured layer can be properly adjusted in accordance with uses, and is ordinarily from 0.1 to 50 μm, preferably from 0.5 to 30 μm, more preferably from 1 to 10 μm. The thickness of the liquid crystal cured layer can be measured by an interference thickness meter, a laser microscope or a stylus-type thickness meter.

Another embodiment of the present invention can also provide an image display device comprising at least one kind selected from the group consisting of the polymer film, the pressure-sensitive adhesive, and the cured layer. The image display device comprises a member containing the compound (I), so that the blue light cutting function can be developed, and an optical film such as a retardation film as well as a display element can be restrained from deteriorating. Also, the compound (I) is excellent in light-selective absorbency to light around a wavelength of 400 nm, so that light around a wavelength of 430 nm as blue light is absorbed with difficulty and the image display device can develop favorable color expression.

EXAMPLES

The present invention will be hereinafter described in further detail by way of examples. '%' and 'part(s)' in examples are % by mass and part(s) by mass unless otherwise specified.

Synthesis Example 1

[Chemical Formula 11]

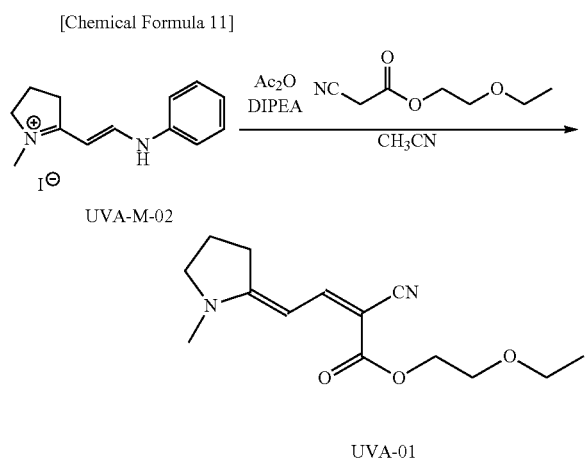

UVA-M-02

UVA-01

The inside of a 200-mL four-necked flask provided with a Dimroth condenser and a thermometer was made into a nitrogen atmosphere, charged with 10 g of compound UVA-M-02 powder synthesized with reference to Patent Literature (JP-A-2014-194508), 3.7 g of acetic anhydride (manufactured by Wako Pure Chemical Industries, Ltd.), 5.8 g of 2-ethoxyethyl cyanoacetate (manufactured by Tokyo Chemical Industry Co., Ltd.) and 60 g of acetonitrile (manufactured by Wako Pure Chemical Industries, Ltd.), and stirred by a magnetic stirrer. To the mixture, 4.7 g of N,N-diisopropylethylamine (hereinafter abbreviated as DIPEA, manufactured by Tokyo Chemical Industry Co., Ltd.) was dropped from a dropping funnel at an internal temperature of 25° C. over 1 hour, and kept at an internal temperature of 25° C. for 2 hours after completion of dropping. Acetonitrile was removed by using a decompression evaporator after completion of the reaction, and an insoluble component produced by adding toluene to the obtained oily matter was filtered out. The filtrate was condensed by using a decompression evaporator again, and the solution after condensation was subject to column chromatography (silica gel) for refinement to obtain an object substance by recrystallization from toluene. The crystal was dried under reduced pressure at 60° C. to thereby obtain a compound UVA-01 as yellow powder in an amount of 5.2 g. The yield was 65%. Also, when absorption maximum wavelength (λmax) was measured by using a spectrophotometer UV-3150 (manufactured by SHIMADZU CORPORATION), the results were such that λmax=389 nm (in 2-butanone), ε(400) was 125 L/(g·cm), and ε(420)/ε(400) was 0.0153.

Then, the following peaks were observed through $^1$H-NMR analysis, so that it was confirmed that the compound UVA-01 was produced.

$^1$H-NMR (CDCl$_3$) δ: 1.21 (t, 3H), 2.10 (quIn. 2H), 2.98-3.04 (m, 5H), 3.54-3.72 (m, 6H), 4.31 (t, 2H), 5.53 (d, 2H), 7.93 (d, 2H)

Synthesis Example 2

[Chemical Formula 12]

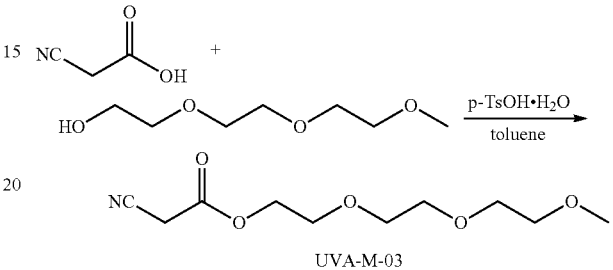

UVA-M-03

The inside of a 100-mL four-necked flask provided with a Dean-Stark pipe, a Dimroth condenser and a thermometer was made into a nitrogen air current condition, charged with 2.0 g of cyanoacetic acid (manufactured by Tokyo Chemical Industry Co., Ltd.), 4.25 g of triethylene glycol monomethyl ether (manufactured by Tokyo Chemical Industry Co., Ltd.), 0.22 g of para-toluenesulfonic acid monohydrate (abbreviated as para-TsOH.H$_2$O, manufactured by Wako Pure Chemical Industries, Ltd.) and 10 g of toluene, and stirred by a magnetic stirrer. The flask was warmed up in an oil bath, subject to boiling reflux at an internal temperature of 110° C. and kept warm for 4 hours while removing by-produced water out of the system. The flask was cooled up to room temperature after completion of the reaction and the toluene solution was washed with pure water. The washing was performed repeatedly until the aqueous layer had a pH of less than 5. The organic layer after washing was concentrated under reduced pressure by using a decompression evaporator to remove toluene, so that a compound UVA-M-03 was obtained as a colorless oily matter in an amount of 4.9 g. The yield was 90%.

[Chemical Formula 13]

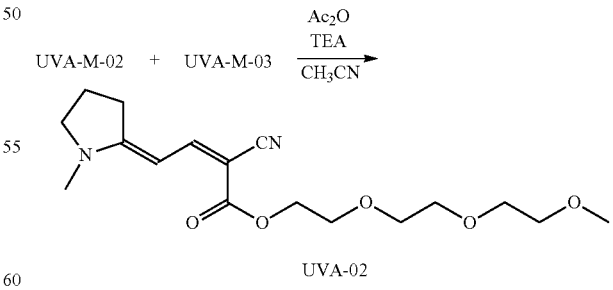

UVA-02

The inside of a 100-mL four-necked flask provided with a Dimroth condenser and a thermometer was made into a nitrogen atmosphere, charged with 2.00 g of the UVA-M-02 powder, 1.41 g of the UVA-M-03 oily matter, 0.64 g of acetic anhydride (manufactured by Wako Pure Chemical Industries, Ltd.) and 26 g of acetonitrile, and stirred by a magnetic stirrer. To the mixture, 0.65 g of triethylamine (manufactured by Wako Pure Chemical Industries, Ltd.) was dropped at an internal temperature of 25° C. over 1 hour, and kept at an internal temperature of 25° C. for 2 hours after completion of dropping. Acetonitrile was removed from the solution by using a decompression evaporator after completion of the reaction, and the obtained oily matter was subjected to column chromatography (silica gel) for refinement to obtain a compound UVA-02 as a yellow oily matter in an amount of 1.1 g. The yield was 53%. Also, when absorption maximum wavelength (λmax) was measured by using a spectrophotometer UV-3150 (manufactured by SHIMADZU CORPORATION), the results were such that λmax=388 nm (in 2-butanone), ε(400) was 95.2 L/(g·cm), and ε(420)/ε(400) was 0.0161.

Synthesis Example 3

[Chemical Formula 14]

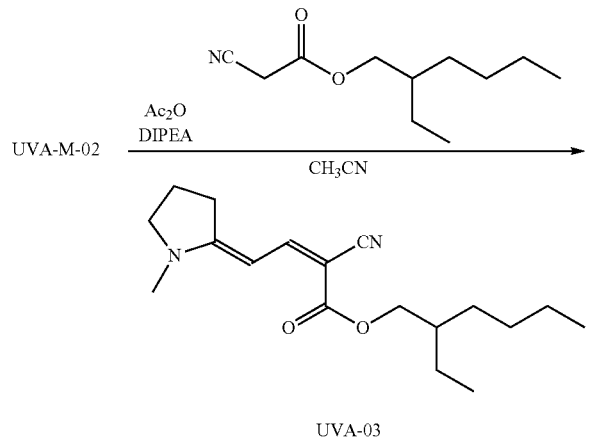

UVA-03

The inside of a 200-mL four-necked flask provided with a Dimroth condenser and a thermometer was made into a nitrogen atmosphere, charged with 10 g of UVA-M-02 powder synthesized with reference to Patent Literature (JP-A-2014-194508), 3.6 g of acetic anhydride (manufactured by Wako Pure Chemical Industries, Ltd.), 6.9 g of 2-ethylhexyl cyanoacetate (manufactured by Tokyo Chemical Industry Co., Ltd.) and 60 g of acetonitrile (manufactured by Wako Pure Chemical Industries, Ltd.), and stirred by a magnetic stirrer. To the mixture, 4.5 g of DIPEA (manufactured by Tokyo Chemical Industry Co., Ltd.) was dropped from a dropping funnel at an internal temperature of 25° C. over 1 hour, and kept at an internal temperature of 25° C. for 2 hours after completion of dropping. Acetonitrile was removed by using a decompression evaporator after completion of the reaction, the solution was subject to column chromatography (silica gel) for refinement, and the solvent was removed from the effluent containing UVA-03 by using a decompression evaporator to obtain yellow crystal. The crystal was dried under reduced pressure at 60° C. to thereby obtain a compound UVA-03 as yellow powder in an amount of 4.6 g. The yield was 50%. When absorption maximum wavelength (λmax) was measured by using a spectrophotometer UV-3150 (manufactured by SHIMADZU CORPORATION), the results were such that λmax=389 nm (in 2-butanone), ε(400) was 108 L/(g·cm), and ε(420)/ε(400) was 0.0132. Then, the following peaks were observed through $^1$H-NMR analysis, so that it was confirmed that the compound UVA-03 was produced.

$^1$H-NMR (CDCl$_3$) δ: 0.87-0.94 (m, 6H), 1.32-1.67 (m, 8H), 1.59-1.66 (m, 2H), 2.09 (quIn. 2H), 3.00 (m, 5H), 3.64 (t, 2H), 4.10 (dd, 2H), 5.52 (d, 2H), 7.87 (d, 2H)

Synthesis Example 4

[Chemical Formula 15]

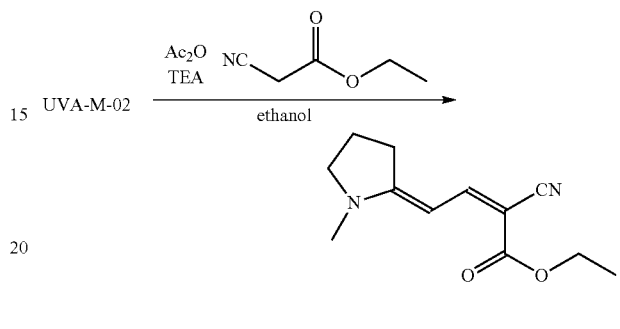

UVA-R01

A compound UVA-R01 was synthesized in accordance with the method described in Patent Literature (DE101 09 243 A1). Refinement was performed by subjecting the solution to column chromatography (silica gel). When absorption maximum wavelength (λmax) was measured by using a spectrophotometer UV-3150 (manufactured by SHIMADZU CORPORATION), the results were such that λmax=389 nm (in 2-butanone), ε(400) was 146 L/(g·cm), and ε(420)/ε(400) was 0.0122. Then, the following peaks were observed through $^1$H-NMR analysis, so that it was confirmed that the compound UVA-R01 was produced.

$^1$H-NMR (CDCl$_3$) δ: 1.31 (t, 3H), 2.09 (quIn. 2H), 3.01 (m, 5H), 3.64 (t, 2H), 4.23 (q, 2H), 5.52 (d, 1H), 7.92 (d, 1H)

Example 1

The compound UVA-01 (50 mg) obtained by the method described in Synthesis Example 1 was mixed with 450 mg of the solvent described below to prepare a 10% by mass solution. A solubility test of UVA-01 was performed at room temperature of 25±3° C. Also, 50 mg of UVA-01 was mixed with 950 mg of the solvent described below to prepare a 5% by mass solution, and the same solubility test was performed. The solubility of the compound UVA-01 was visually confirmed in 60 minutes after preparation of each solution. The results are shown in Table 1. Incidentally, the criteria for evaluation of the test results are as follows.

A: soluble by 10% by mass or more
B: soluble by 5% by mass or more and less than 10% by mass
C: soluble by less than 5% by mass
(Used Solvents)
2-butanone (manufactured by KANTO CHEMICAL CO., INC., hereinafter abbreviated as MEK)
2-propanol (manufactured by NACALAI TESQUE, INC., hereinafter abbreviated as IPA)
toluene (manufactured by NACALAI TESQUE, INC., hereinafter abbreviated as TOL)
ethyl acetate (manufactured by NACALAI TESQUE, INC., hereinafter abbreviated as EAC)
chloroform (manufactured by KANTO CHEMICAL CO., INC., hereinafter abbreviated as CHF)
propylene glycol monomethyl ether acetate (manufactured by Tokyo Chemical Industry Co., Ltd., hereinafter abbreviated as PGMEA)

Examples 2 and 3

The solubility test was performed in the same manner as in Example 1 except for replacing UVA-01 with UVA-02 or UVA-03. The results are shown in Table 1.

Comparative Example 1

The solubility test was performed in the same manner as in Example 1 except for replacing UVA-01 with UVA-R01. The results are shown in Table 1.

TABLE 1

|  | Light-selective absorptive compound | Solubility in various solvents | | | | | |
|---|---|---|---|---|---|---|---|
|  |  | MEK | IPA | TOL | EAC | CHF | PGMEA |
| Example 1 | UVA-01 | A | A | A | A | A | A |
| Example 2 | UVA-02 | A | A | A | A | A | A |
| Example 3 | UVA-03 | A | A | A | A | A | B |
| Comparative Example 1 | UVA-R01 | C | C | C | C | C | C |

In the following polymerization examples, the measurement of weight-average molecular weight and number-average molecular weight was performed in terms of standard polystyrene under conditions of a sample concentration of 5 mg/mL, a sample introduction amount of 100 μL, a temperature of 40° C. and a flow velocity of 1 mL/minute by using tetrahydrofuran as an eluate while five pieces in total of four pieces of "TSK gel XL" (manufactured by Tosoh Corporation) and one piece of "Shodex GPC KF-802" (manufactured by Showa Denko K.K.) were disposed as columns in serial connection in a gel permeation chromatography (hereinafter abbreviated as GPC) apparatus (GPC-8120, manufactured by Tosoh Corporation).

Polymerization Example 1

A mixed solution of 81.8 parts of ethyl acetate as a solvent, 70.4 parts of butyl acrylate, 20.0 parts of methyl acrylate and 8.0 parts of 2-phenoxyethyl acrylate as monomers (A-1), 1.0 part of 2-hydroxyethyl acrylate as a monomer (A-2), and 0.6 parts of acrylic acid as a monomer (A-3) was charged into a reaction vessel provided with a condenser, a nitrogen introduction pipe, a thermometer and a stirrer. The internal temperature was raised to 55° C. while the air in the apparatus was replaced with nitrogen gas so as to be oxygen-free. Thereafter, to the mixture was added whole amount of a solution in which 0.14 parts of 2,2'-azobisisobutyronitrile (polymerization initiator) was dissolved in 10 parts of ethyl acetate. The mixture was retained at this temperature for 1 hour after addition of the polymerization initiator, and subsequently ethyl acetate was continuously added into the reaction vessel at an addition rate of 17.3 parts/hr while the internal temperature was maintained at 54 to 56° C., and the addition of ethyl acetate was stopped at a point of time when the concentration of acrylic resin to be produced became 35%, and further the reaction vessel was retained at this temperature until 12 hours passed from the start of the addition of ethyl acetate. Finally, the concentration of acrylic resin was adjusted to 20% by adding ethyl acetate to prepare an ethyl acetate solution of acrylic resin. With regard to the obtained acrylic resin, the weight-average molecular weight $M_w$ in terms of polystyrene by GPC was 1420000 and $M_w/M_n$ was 5.2. This obtained acrylic resin is regarded as an acrylic resin A.

Polymerization Example 2

A mixed solution of 81.8 parts of ethyl acetate as a solvent, 96.0 parts of butyl acrylate as a monomer (A-1), and 4.0 parts of acrylic acid as a monomer (A-3) was charged into a reaction vessel provided with a condenser, a nitrogen introduction pipe, a thermometer and a stirrer. The internal temperature was raised to 55° C. while the air in the apparatus was replaced with nitrogen gas so as to be oxygen-free. Thereafter, to the mixture was added whole amount of a solution in which 0.14 parts of 2,2'-azobisisobutyronitrile (polymerization initiator) was dissolved in 10 parts of ethyl acetate. The mixture was retained at this temperature for 1 hour after addition of the polymerization initiator, and subsequently ethyl acetate was continuously added into the reaction vessel at an addition rate of 17.3 parts/hr while the internal temperature was maintained at 54 to 56° C., and the addition of ethyl acetate was stopped at a point of time when the concentration of acrylic resin to be produced became 35%, and further the reaction vessel was retained at this temperature until 12 hours passed from the start of the addition of ethyl acetate. Finally, the concentration of acrylic resin was adjusted to 20% by adding ethyl acetate to prepare an ethyl acetate solution of acrylic resin. With regard to the obtained acrylic resin, the weight-average molecular weight $M_w$ in terms of polystyrene by GPC was 756000 and $M_w/M_n$ was 4.1. This obtained acrylic resin is regarded as an acrylic resin B.

The list of the monomer composition, the weight-average molecular weight $M_w$ and $M_w/M_n$ of each of the obtained acrylic resin A and B in Polymerization Examples 1 and 2 is shown in Table 2. Incidentally, the abbreviation of the monomer composition in the table denotes each of the following monomers.

Monomer (A-1)
BA: butyl acrylate
MA: methyl acrylate
PEA: 2-phenoxyethyl acrylate
Monomer (A-2)
HEA: 2-hydroxyethyl acrylate
Monomer (A-3)
AA: acrylic acid

TABLE 2

|  | Monomer composition (part(s)) | | | | | Molecular weight ($M_w$) | Molecular-weight distribution ($M_w/M_n$) | Acrylic resin |
|---|---|---|---|---|---|---|---|---|
|  | (A-1) | | | (A-2) | (A-3) | | | |
|  | BA | MA | PEA | HEA | AA | | | |
| Polymerization Example 1 | 70.4 | 20.0 | 8.0 | 1.0 | 0.6 | 1420000 | 5.2 | A |
| Polymerization Example 2 | 96.0 | — | — | — | 4.0 | 756000 | 4.1 | B |

Next, a pressure-sensitive adhesive resin was prepared by using the acrylic resin produced in Polymerization Example 1 or 2, and applied to an optical film. Incidentally, each of the following was used as a crosslinking agent and a silane compound.

[Crosslinking Agent]

CORONATE L: a solution of a trimethylolpropane adduct of tolylene diisocyanate in ethyl acetate (solid content concentration of 75%), manufactured by Nippon Polyurethane Industry Co., Ltd.

TAKENATE D-110N: a solution of a trimethylolpropane adduct of xylylene diisocyanate in ethyl acetate (solid content concentration of 75%), manufactured by Mitsui Chemicals, Inc. (hereinafter abbreviated as D110N)

[Silane Compound]

KBM-403: 3-glycidoxypropyltrimethoxysilane manufactured by Shin-Etsu Chemical Co., Ltd. (hereinafter abbreviated as KBM-403)

Production Examples 1 to 8

(a) Preparation of Pressure-sensitive Adhesive Composition

An acrylic resin, crosslinking agent, silane compound and light-selective absorptive compound described in the following Table 3 were mixed to produce each of pressure-sensitive adhesive compositions (1) to (8). The addition part(s) of each component is described in Table 3 as part(s) by mass with respect to 100 parts by mass of the solid content in the acrylic resin produced in Polymerization Examples 1 and 2. Here, 2-butanone was added so that the solid content concentration of each of the pressure-sensitive adhesive compositions (1) to (8) was 14%, and the mixture was stirred at 300 rpm for 30 minutes by using a stirrer (THREE-ONE MOTOR BL-300, manufactured by Yamato Scientific Co., Ltd.) to prepare the pressure-sensitive adhesive compositions (1) to (8).

(b) Production of Pressure-sensitive Adhesive Sheet

Each of the pressure-sensitive adhesive compositions (1) to (8) prepared in (a) above was applied onto a releasing treatment surface of a releasing-treated polyethylene terephthalate film (SP-PLR382050, manufactured by LINTEC Corporation, hereinafter abbreviated as a separator) by an applicator so that the pressure-sensitive adhesive layer thickness after drying was 20 μm, and thereafter dried at 100° C. for 1 minute to produce pressure-sensitive adhesive sheets (1) to (8).

Example 4

The pressure-sensitive adhesive sheet (1) was subject to a heat shock-resistant test such that a process of cooling to −40° C. from a state of heating to 70° C. and subsequently heating to 70° C. as a cycle (30 minutes) was repeated by 100 cycles in total (hereinafter abbreviated as 'HS-resistant'). The pressure-sensitive adhesive sheet after the test was visually observed to evaluate the presence or absence of crystal precipitation in the sheet in accordance with the following standard. A sample for evaluation was produced 5 sheets for one condition and the evaluation was conducted along the following criteria. The evaluation results are shown in Table 4.

[Criteria for Evaluation of Crystal Precipitation]

A: Appearance changes such as lifting, peeling and foaming are scarcely confirmed B: Appearance changes such as lifting, peeling and foaming are remarkably confirmed Examples 5 to 9 and Comparative Examples 2 to 3

The HS-resistant test was performed in the same manner as in Example 3 except for replacing the pressure-sensitive adhesive sheet (1) with each of the pressure-sensitive adhe-

TABLE 3

| | Composition of pressure-sensitive adhesive composition (parts by mass) | | | | | | |
|---|---|---|---|---|---|---|---|
| | Acrylic | Crosslinking agent | | Silane compound | | Light-selective absorptive compound | |
| | resin Name | Name | Added amount | Name | Added amount | Name | Added amount |
| Production Example 1 [pressure-sensitive adhesive sheet (1)] | A | CORONATE L | 0.50 | KBM-403 | 0.50 | UVA-01 | 0.61 |
| Production Example 2 [pressure-sensitive adhesive sheet (2)] | A | CORONATE L | 0.50 | KBM-403 | 0.50 | UVA-02 | 1.41 |
| Production Example 3 [pressure-sensitive adhesive sheet (3)] | A | CORONATE L | 0.50 | KBM-403 | 0.50 | UVA-03 | 1.20 |
| Production Example 4 [pressure-sensitive adhesive sheet (4)] | A | CORONATE L | 0.50 | KBM-403 | 0.50 | UVA-R01 | 0.75 |
| Production Example 5 [pressure-sensitive adhesive sheet (5)] | B | CORONATE L | 0.50 | KBM-403 | 0.50 | UVA-01 | 0.61 |
| Production Example 6 [pressure-sensitive adhesive sheet (6)] | B | CORONATE L | 0.50 | KBM-403 | 0.50 | UVA-02 | 1.41 |
| Production Example 7 [pressure-sensitive adhesive sheet (7)] | B | CORONATE L | 0.50 | KBM-403 | 0.50 | UVA-03 | 1.20 |
| Production Example 8 [pressure-sensitive adhesive sheet (8)] | B | CORONATE L | 0.50 | KBM-403 | 0.50 | UVA-R01 | 0.75 | sive sheets described in the following Table 4 to evaluate the presence or absence of crystal precipitation in the pressure-sensitive adhesive sheet after the test. The evaluation results are shown in Table 4.

TABLE 4

| | Pressure-sensitive adhesive sheet | A(400) | A(420) | A(420)/A(400) | Crystal precipitation evaluation |
|---|---|---|---|---|---|
| Example 4 | Pressure-sensitive adhesive sheet (1) | 2.13 | 0.21 | 0.097 | A |
| Example 5 | Pressure-sensitive adhesive sheet (2) | 2.89 | 0.24 | 0.083 | A |
| Example 6 | Pressure-sensitive adhesive sheet (3) | 3.40 | 0.25 | 0.074 | A |
| Example 7 | Pressure-sensitive adhesive sheet (5) | 2.14 | 0.20 | 0.093 | A |
| Example 8 | Pressure-sensitive adhesive sheet (6) | 2.90 | 0.23 | 0.079 | A |
| Example 9 | Pressure-sensitive adhesive sheet (7) | 3.41 | 0.23 | 0.062 | A |
| Comparative Example 2 | Pressure-sensitive adhesive sheet (4) | 2.77 | 0.23 | 0.082 | B |
| Comparative Example 3 | Pressure-sensitive adhesive sheet (8) | 2.76 | 0.21 | 0.076 | B |

In the Example 4 through 9, a number of the sample in which appearance changes such as lifting, peeling and foaming are scarcely confirmed was 4 or more. On the other hand, in the Comparative Example 2 and 3, a number of the sample in which appearance changes such as lifting, peeling and foaming are remarkably confirmed was 2 or more. These results show that the compound of the present invention is superior in affinity with hydrophobic substances and in solubility in various solvents.

Example 10

EBECRYL4858 (20 parts) (manufactured by DAICEL-ALLNEX LTD.), 0.80 parts of UVA-01 obtained by the method described in Synthesis Example 1, 0.21 parts of Irgacure-184 (manufactured by BASF JAPAN), 26 parts of ortho-xylene (manufactured by KANTO CHEMICAL CO., INC.) and 24 parts of N-methyl-2-pyrrolidone (manufactured by KANTO CHEMICAL CO., INC.) were mixed and stirred at room temperature for 2 hours to produce a uniform solution. The obtained solution was coated on a glass substrate by using a spin coat, dried on a hot plate at 110° C. for 1 minute, and subsequently irradiated with ultraviolet rays at an radiation intensity of 36 mW/cm² for 30 seconds under a nitrogen atmosphere by using a high-pressure mercury lamp to produce a cured layer.

The thickness of the obtained cured layer was measured by a laser microscope (LEXT OLS3000, manufactured by Olympus Corporation), and was 2.3 μm. The turbidity was measured by using a haze meter (HZ-2, manufactured by Suga Test Instruments Co., Ltd.), and was 1.3. Also, the absorption spectrum of the obtained cured layer was measured, and was A (400)=1.41, A (420)=0.048 and A (420)/A (400)=0.034 (measurement apparatus: UV-3150, manufactured by SHIMADZU CORPORATION).

The in-plane retardation value was measured at a wavelength of 550 nm by using a birefringence measuring device (KOBRA-WR, manufactured by Oji Scientific Instruments Co., Ltd.), and was 1 nm.

Therefore, it was confirmed that the obtained cured layer satisfied all of the following formulae (1) to (3):

$$0 \text{ nm} \leq Re < 10 \text{ nm} \quad \text{Formula (1)}$$

$$A(420)/A(400) \leq 0.4 \quad \text{Formula (2)}$$

$$Hz \leq 3 \quad \text{Formula (3)}.$$

What is claimed is:

1. A compound represented by formula (I) below:

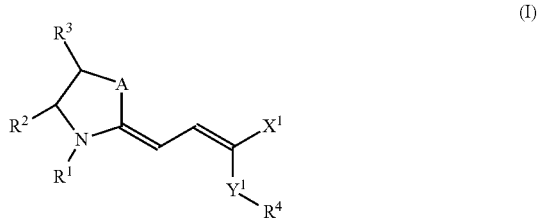

(I)

wherein in the formula (I):
A denotes a methylene group, a secondary amino group, an oxygen atom or a sulfur atom,
$R^1$ denotes a hydrogen atom or an alkyl group with a carbon number of 1 to 10; and when the alkyl group has at least one methylene group, at least one of the methylene groups is optionally substituted with an oxygen atom or a sulfur atom,
$R^2$ and $R^3$ independently denote a hydrogen atom or an alkyl group with a carbon number of 1 to 12,
$R^4$ denotes an alkyl group with a carbon number of 3 to 50 or an alkyl group with a carbon number of 3 to 50 having at least one methylene group, wherein at least one of the methylene groups is substituted with an oxygen atom, and a substituent may be bonded to a carbon atom in the alkyl group,
$X^1$ denotes an electron-withdrawing group,
$Y^1$ denotes —CO—, —COO—, —OCO—, —O—, —S—, —NR$^5$—, —NR$^6$CO— or —CONR$^7$—, and $R^5$, $R^6$ and $R^7$ independently denote a hydrogen atom, an alkyl group with a carbon number of 1 to 6 or a phenyl group.

2. The compound according to claim 1, wherein $R^4$ in the formula (I) is an alkyl group with a carbon number of 3 to 12 having a branched structure.

3. The compound according to claim 1, wherein the compound represented by the formula (I) is represented by formula (I-I) below:

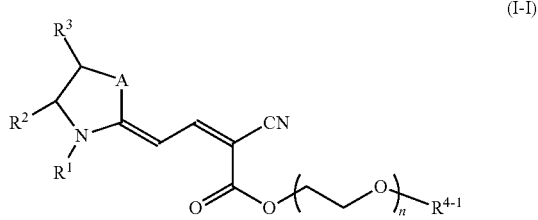

(I-I)

wherein in formula (I-I):
$R^{4-1}$ denotes an alkyl group with a carbon number of 1 to 6,
n denotes an integer of 1 to 10, and
A, $R^1$, $R^2$ and $R^3$ are the same as in the formula (I).

4. The compound according to claim 3, wherein the compound represented by the formula (I-I) is represented by formula (I-II) below:

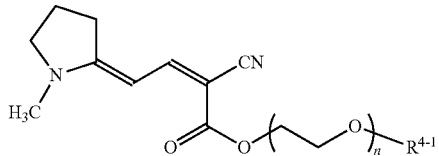

(I-II)

wherein in formula (I-II): $R^{4-1}$ and n are the same as in the formula (I-I).

5. A polymer composition comprising the compound according to claim 1 and a polymer.

6. The polymer composition according to claim 5, wherein the polymer is at least one kind selected from the group consisting of poly(meth)acrylate, polyurethane, polyester, polycarbonate, polycycloolefin and triacetyl cellulose.

7. The polymer composition according to claim 5, wherein the polymer is a copolymer which has as a constitutional unit a (meth)acrylate monomer (A-1) represented by formula (A-1) below:

(A-1)

wherein in formula (A-1):
$R^p$ denotes a hydrogen atom or a methyl group,
$R^q$ denotes an alkyl group or an aralkyl group with a carbon number of 1 to 20, wherein a hydrogen atom constituting the alkyl group or the aralkyl group is optionally substituted with —O—$(C_2H_4O)n$—$R^r$, n denotes an integer of 0 to 4, and $R^r$ denotes an alkyl group with a carbon number of 1 to 12 or an aryl group with a carbon number of 1 to 12 and a (meth)acrylic monomer (A-2) having a hydroxyl group, and which is poly(meth)acrylate with a weight-average molecular weight of 500000 to 2000000; and
the polymer composition contains 0.01 to 5 parts by mass of a crosslinking agent and 0.01 to 10 parts by mass of the compound of formula (I) with respect to 100 parts by mass of the polymer.

8. A polymer film comprising the polymer composition according to claim 5.

9. A pressure-sensitive adhesive comprising the polymer composition according to claim 7.

10. A photopolymerizable composition comprising a monomer having a photopolymerizable functional group, a photopolymerization initiator, a solvent and the compound according to claim 1.

11. A cured layer comprising a cured material of the photopolymerizable composition according to claim 10, which satisfies formulae (1) to (3) below:

$$0\,nm \leq Re < 10\ nm \quad (1)$$

$$A(420)/A(400) \leq 0.4 \quad (2)$$

$$Hz \leq 3 \quad (3)$$

wherein:
Re in formula (1) denotes an in-plane retardation value at a wavelength of 550 nm,
A(420) in the formula (2) denotes absorbance at 420 nm and A(400) denotes absorbance at 400 nm, and
Hz in the formula (3) denotes turbidity.

12. An image display device comprising the polymer film according to claim 8.

13. An image display device comprising the pressure-sensitive adhesive according to claim 9.

14. An image display device comprising the cured layer according to claim 11.

* * * * *